(12) United States Patent
Nakamura et al.

(10) Patent No.: US 8,673,595 B2
(45) Date of Patent: Mar. 18, 2014

(54) SAMPLE ANALYSIS METHOD AND ASSAY KIT USED THEREIN

(75) Inventors: Naoko Nakamura, Machida (JP); Koji Hashimoto, Atsugi (JP); Nobuhiro Gemma, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 13/340,572

(22) Filed: Dec. 29, 2011

(65) Prior Publication Data

US 2012/0171673 A1 Jul. 5, 2012

Related U.S. Application Data

(63) Continuation of application No. PCT/JP2009/061878, filed on Jun. 29, 2009.

(51) Int. Cl.
*C12P 19/34* (2006.01)
(52) U.S. Cl.
USPC ...................................... 435/91.2; 435/91.21
(58) Field of Classification Search
USPC ............................................ 435/91.2, 91.21
See application file for complete search history.

(56) References Cited

U.S. PATENT DOCUMENTS

| 5,776,672 | A | 7/1998 | Hashimoto et al. |
| 5,972,692 | A | 10/1999 | Hashimoto et al. |
| 7,488,581 | B2 | 2/2009 | Nakamura et al. |
| 7,919,252 | B2 | 4/2011 | Nakamura et al. |
| 2004/0126764 | A1 | 7/2004 | Lasken et al. |
| 2006/0194223 | A1 | 8/2006 | Andreoli et al. |

FOREIGN PATENT DOCUMENTS

| JP | 10-146183 | | 6/1998 |
| JP | 2005-143492 | | 6/2005 |
| JP | 2006-512094 | | 4/2006 |
| JP | 2006-526399 | | 11/2006 |
| WO | WO 2005047533 | * | 5/2005 |

OTHER PUBLICATIONS

Liang et al., Analytical Chemisry, vol. 84, pp. 3758-3763, 2012.*
International Search Report, dated Aug. 25, 2009, issued in PCT/JP2009/061878.
Ann Caviani Pease, et al. "Light-generated oligonucleotide arrays for rapid DNA sequence analysis", Proc. Natl. Acad. Sci. USA, Biochemistry, vol. 91, May 1994, pp. 5022-5026.

* cited by examiner

*Primary Examiner* — Cynthia B Wilder
(74) *Attorney, Agent, or Firm* — Oblon, Spivak, McClelland, Maier & Neustadt, L.L.P.

(57) ABSTRACT

One embodiment is related to a method of analyzing plural samples. The method includes amplifying a plurality of samples using a first primer and second primer, wherein the first primer includes a tag sequence having a sequence different from a sample to one another and wherein a second primer used in pair with the first primer in independent reaction systems for the respective samples to obtain an amplified product in which the tag sequence is introduced, mixing amplified products obtained in the plurality of reaction systems, making the mixed amplified product react with a nucleic acid probe immobilized on a substrate, and detecting the amount of hybridization that has occurred.

7 Claims, 15 Drawing Sheets

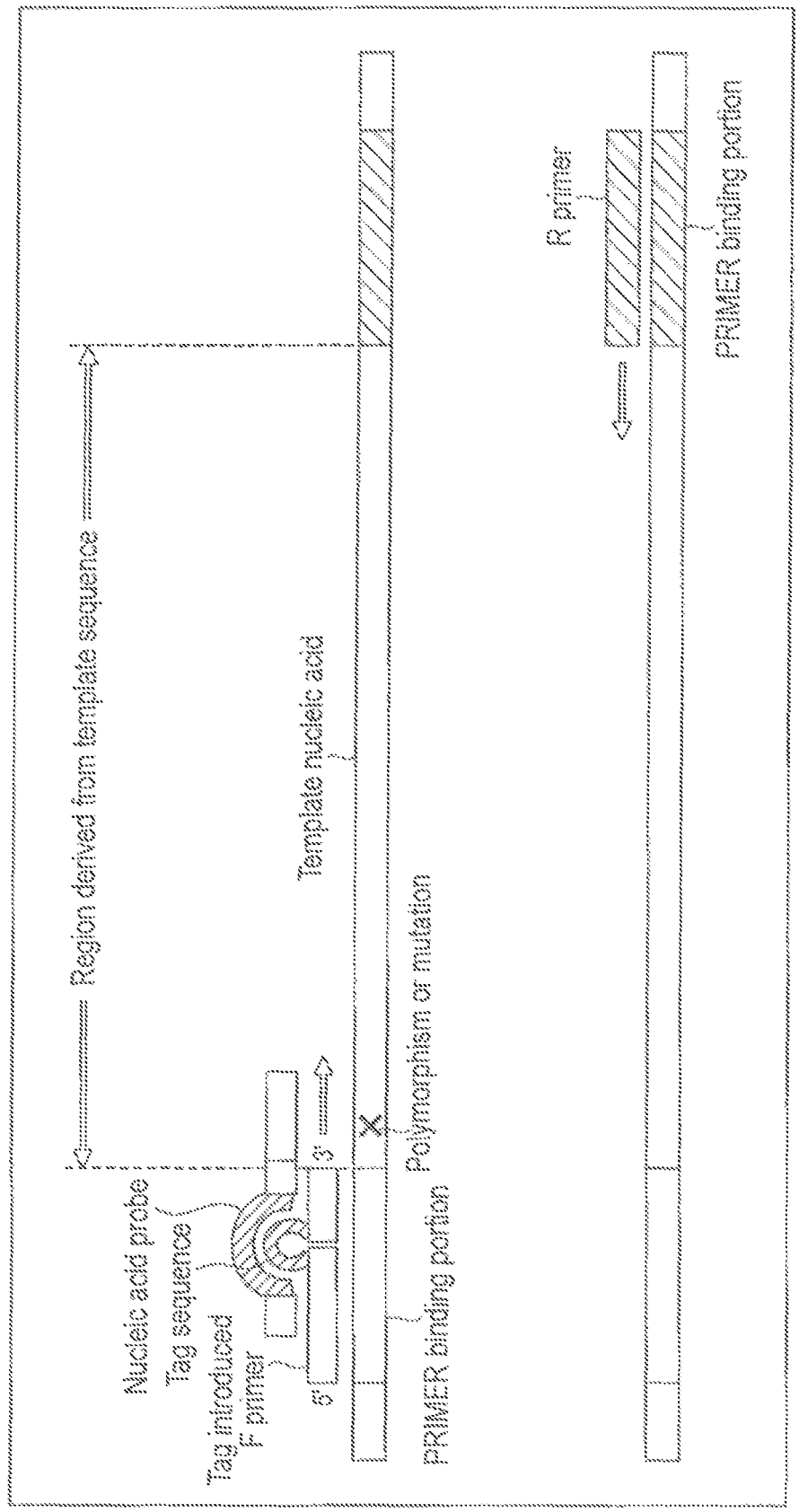
F I G. 1

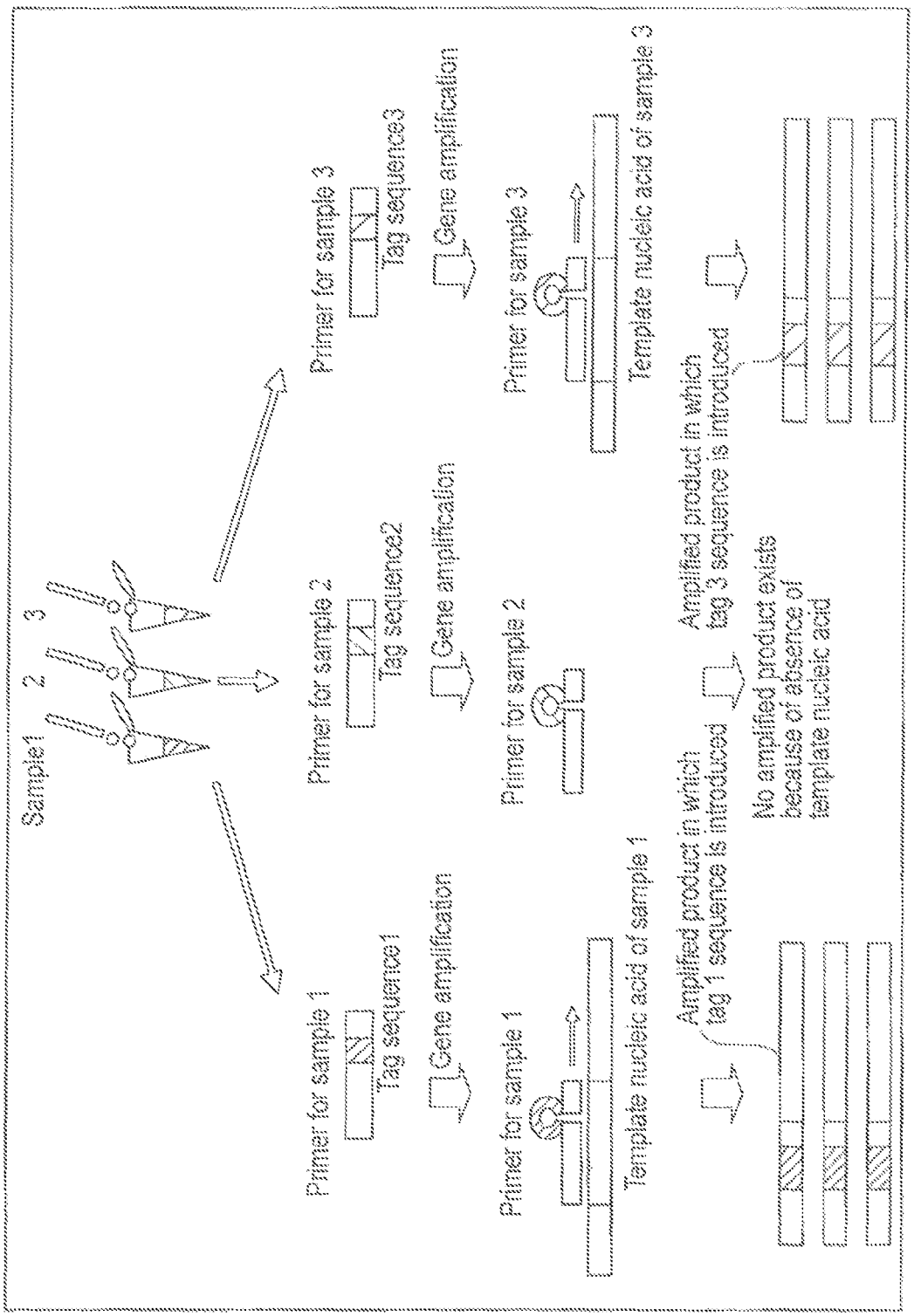
F I G. 2

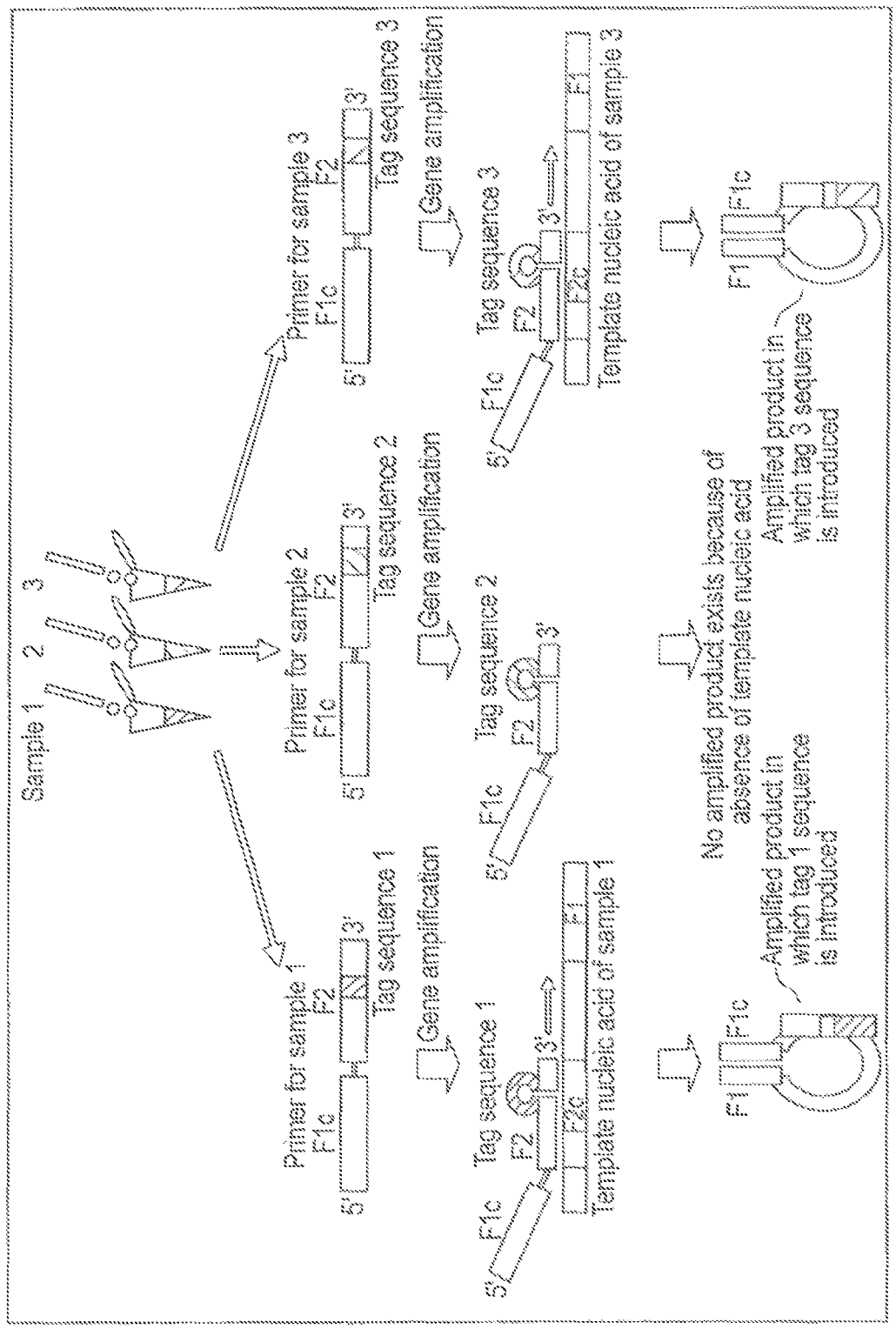
F I G. 7

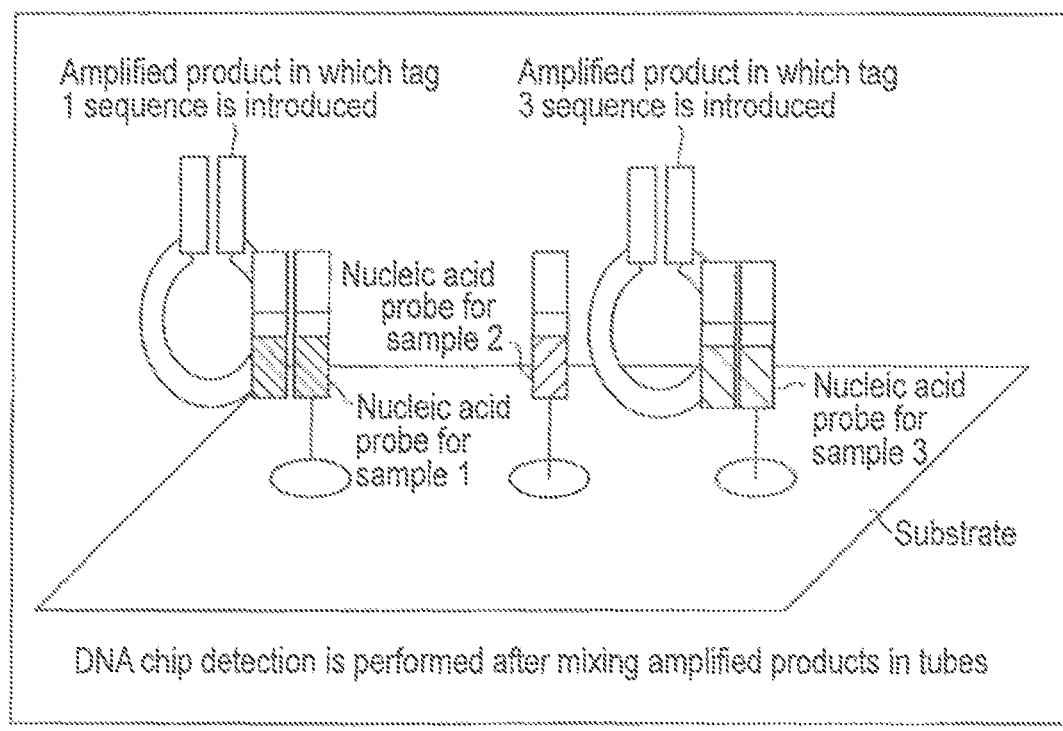
F I G. 8

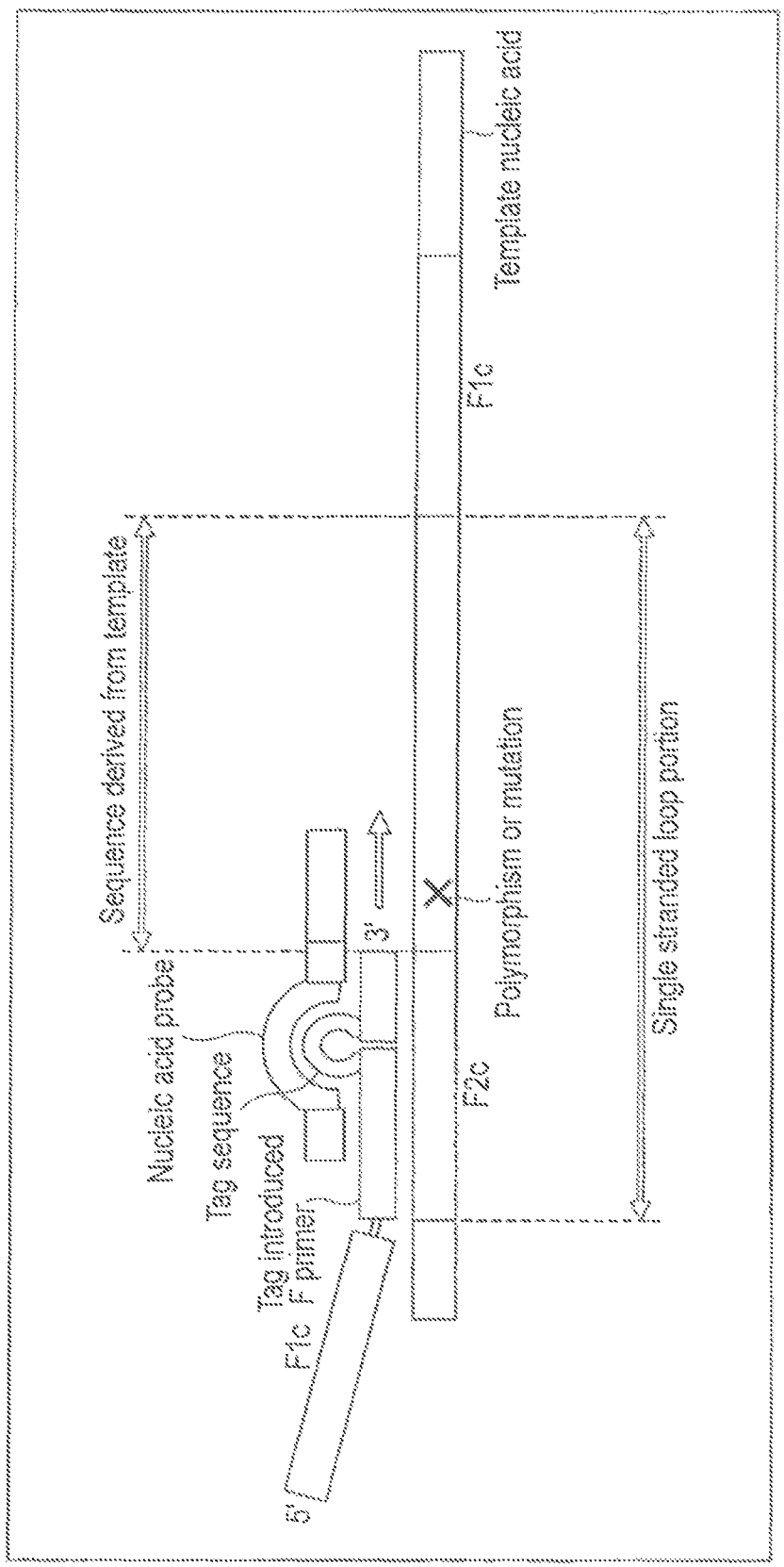
F I G. 9

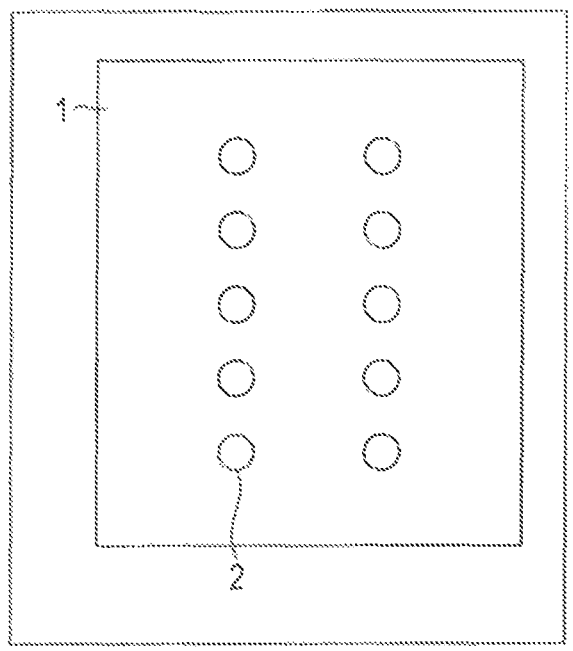
F I G. 11
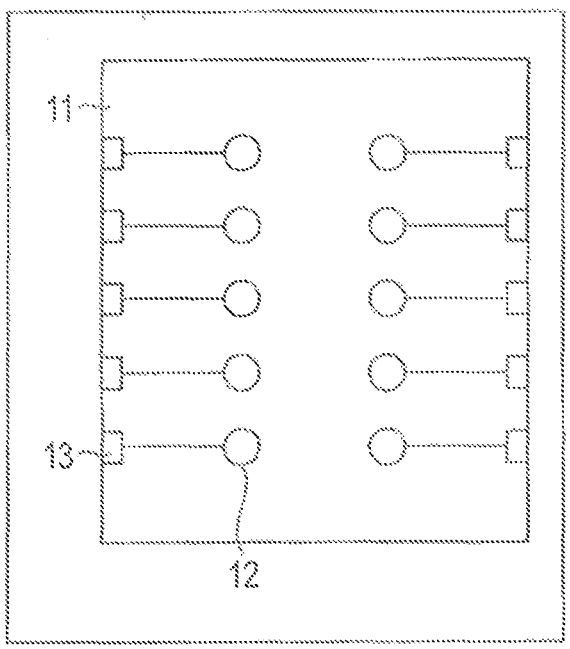
F I G. 12

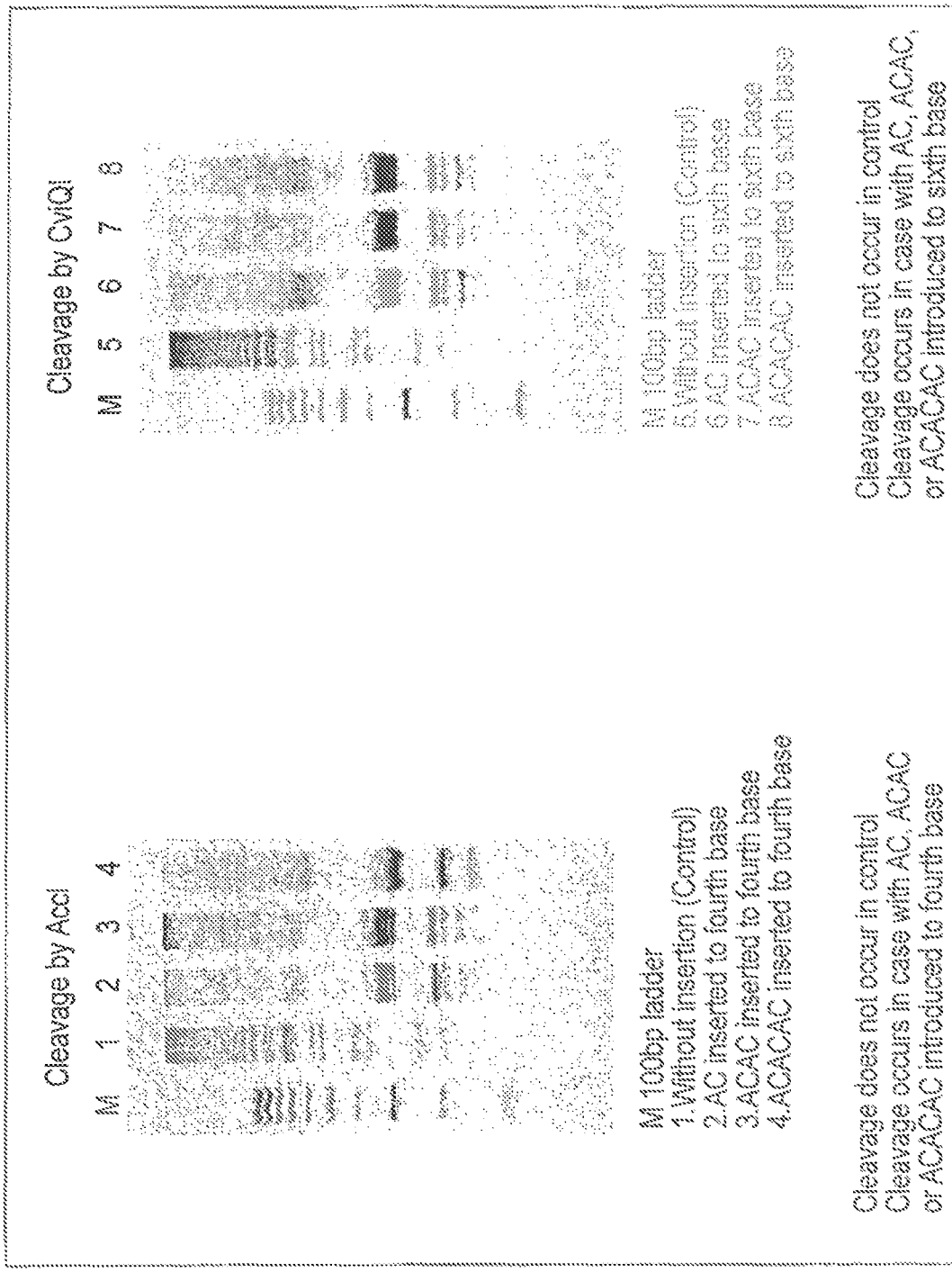
F I G. 13

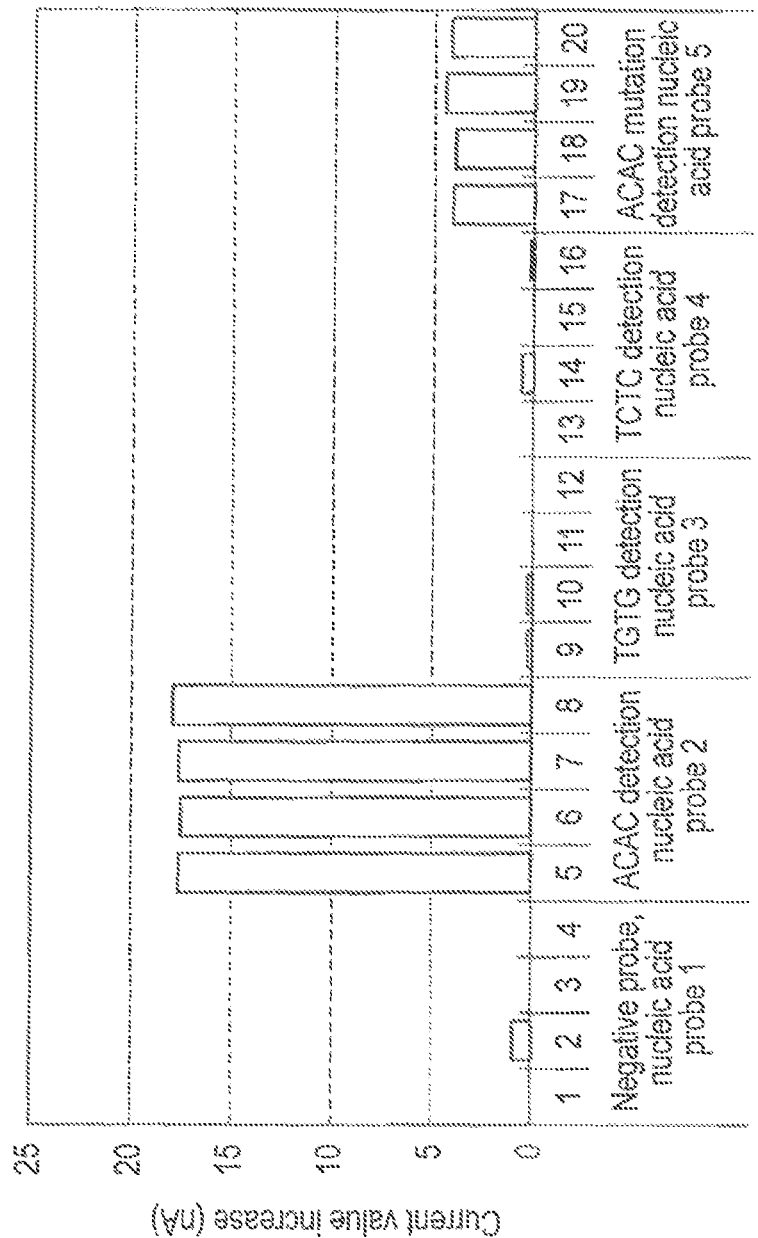
F I G. 14A

US 8,673,595 B2

SAMPLE ANALYSIS METHOD AND ASSAY KIT USED THEREIN

CROSS REFERENCE TO RELATED APPLICATIONS

This application is a Continuation Application of PCT Application No. PCT/JP2009/061878, filed Jun. 29, 2009, the entire contents of which are incorporated herein by reference.

FIELD

Embodiments described herein relate generally to a nucleic acid analysis method.

BACKGROUND

A DNA chip is a device in which 10 to $10^5$ types of DNA nucleic acid strands serving as probes are immobilized on a slide glass or silicon substrate several cm square. To analyze a sample using a DNA chip, first, the contained nucleic acids are labeled by a fluorescent dye, a radioisotope, or the like, and then made to react with the probes on the chip. If the nucleic acids in the sample contain a nucleic acid complementary to a probe on the chip, hybridization occurs. Each probe immobilized on the chip has a known sequence and immobilization position. Hence, specifying the position on the chip where a signal derived from the label is obtained enables to determine the sequence of the nucleic acid contained in the sample (non-patent literature 1). The DNA chip is a device (testing tool) of enormous usefulness in analyzing a number of genes at once for one specimen. Normally, one chip is used for one specimen. To check the expression level difference between two specimens, one chip is used for two specimens.

On the other hand, for example, in the field of infectious diseases, the number of samples may be large, although the number of genes to be checked is small. However, since it is conventionally necessary to use a lot of chips in accordance with the number of samples, the test cost including the chip, labor, and time is high.

BRIEF DESCRIPTION OF THE DRAWINGS

FIG. 1 is a view showing a tag sequence-introduced primer and a nucleic acid probe.

FIG. 2 is a scheme diagram showing an amplification step.

FIG. 7 is a scheme diagram showing an amplification step.

FIG. 8 is a view showing a detection step.

FIG. 9 is a view showing a primer.

FIG. 11 is a plan view of a DNA chip.

FIG. 12 is a plan view of another DNA chip.

FIG. 13 is a view showing a result of amplified product cleavage by restriction enzyme processing.

FIG. 14A is a graph showing a result of detection of plural samples.

DETAILED DESCRIPTION

Figure 3:
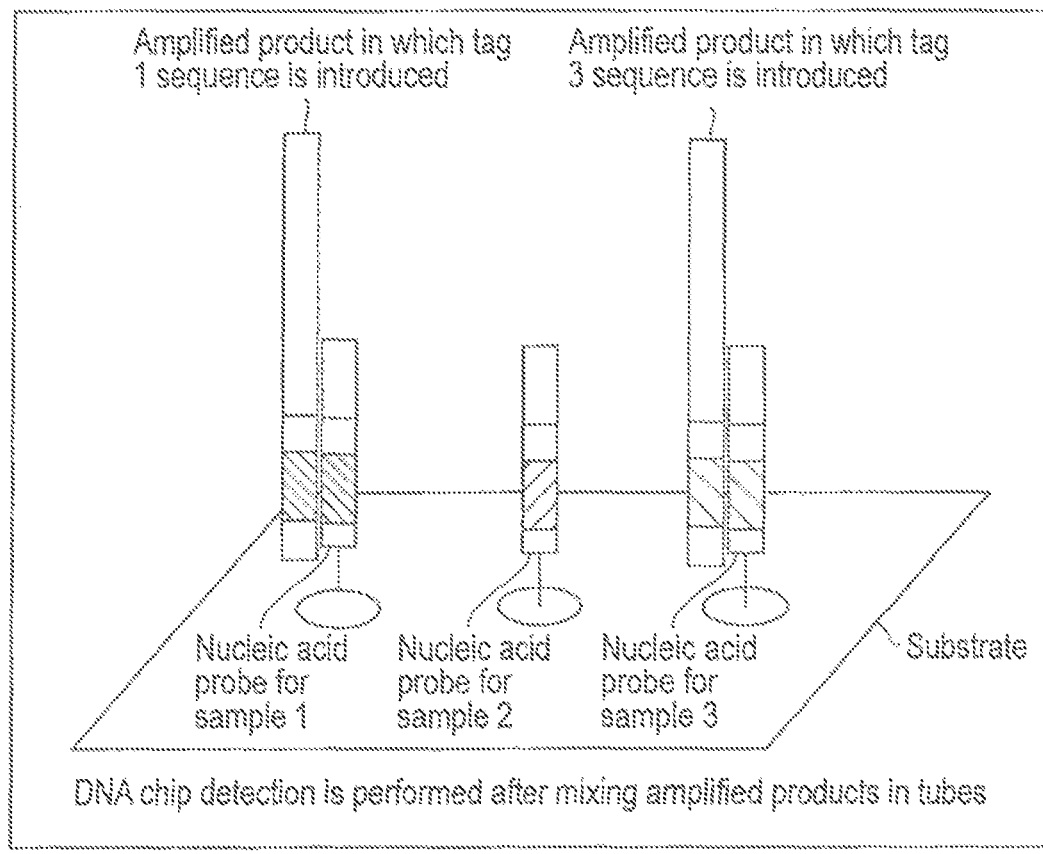
FIG. 3 is a view showing a detection step.

One embodiment is related to a method of analyzing plural samples by amplifying a plurality of samples using a first primer including a tag sequence having a sequence different for said every sample one another, and a second primer used in pair with the first primer in independent reaction systems for the respective samples, mixing amplified products obtained in the plurality of reaction systems and having the tag sequences introduced, making the mixed amplified product react with a nucleic acid probe immobilized on a substrate, and detecting the amount of hybridization that has occurred.

[Definitions]

The term "nucleic acid" used in this specification collectively means substances such as DNA, RNA, PNA, LNA, S-oligo, and methyl phosphonate oligo whose partial structure can be expressed by a base sequence.

A "sample" is the target for which the analysis method according to the embodiment should be performed, and need only be a specimen that can contain a nucleic acid. The sample is preferably in a state that does not impede amplification reaction and/or hybridization reaction. For example, to use a material obtained from a living body as a sample according to the embodiment, the material is preprocessed using a certain means known by itself. For example, the sample may be a liquid. In this case, the sample may be called a "test liquid". Hence, a "test liquid" can be interpreted as a solution that can contain a nucleic acid or a template nucleic acid.

The terms "multiple samples" and "plural samples" represent two or more samples and can interchangeably be used.

A nucleic acid contained in a sample is called a "sample nucleic acid". Out of the sample nucleic acid, a sequence to be amplified by a primer according to the embodiment is called a "template sequence". A nucleic acid including a template sequence is called a "template nucleic acid" or a "template". A partial sequence included in a template nucleic acid is called a "partial nucleic acid sequence". The partial nucleic acid sequence is a sequence or base to be analyzed. A primer according to the embodiment is designed to amplify a region including a partial nucleic acid sequence. The partial nucleic acid sequence can either equal a template sequence or be included in a template sequence.

A "target nucleic acid" is an amplified product obtained by amplifying a template nucleic acid or a template sequence using a forward primer and a reverse primer according to the embodiment. A target nucleic acid partially includes a target sequence.

A "target sequence" is formed from a tag sequence and a partial sequence of a template sequence. The target sequence is used to detect a target nucleic acid using a nucleic acid probe.

A "nucleic acid probe" is a nucleic acid including a sequence complementary to a target sequence. The nucleic acid probe is used while being immobilized on a solid phase such as a substrate and forms a hybrid with an amplified product including a region derived from a template sequence.

A "region derived from a template sequence" means, out of a region amplified by a primer, a region other than that bound with the primer on which the template sequence is reflected. To detect a genetic polymorphism or a genetic mutation, the region is designed to include that part.

A "DNA chip" is a device for analyzing a nucleic acid using the hybridization reaction between the nucleic acid to be detected and a nucleic acid probe having a sequence complimentary to the nucleic acid to be detected. The term "DNA chip" is synonymous with the terms such as "nucleic acid chip", "microarray", and "DNA array" that are generally used, and they are interchangeably be used.

"Analyzing multiple samples" means simultaneously analyzing plural samples. "Analyzing a plurality of nucleic acid sequences in a sample" means simultaneously analyzing a plurality of partial nucleic acid sequences included in one sample. The plurality of partial nucleic acid sequences to be analyzed simultaneously can be either included in one template nucleic acid or respectively included in different types of test nucleic acids contained in a sample.

The analysis items can include, for example, detection of a specific nucleic acid such as a gene derived from a virus and/or a bacterium, measurement of a gene expression level, identification of a genotype for a polymorphism and/or detection of the presence/absence of a mutation. The items are not limited to those.

[Embodiment]

Now embodiments will be further described.

FIG. 1 is a view showing a tag sequence-introduced primer and a nucleic acid probe.

<Primer>

As exemplified by the tag-introduced F primer in FIG. 1, a sequence to be bound to the primer binding portion of a template nucleic acid and a tag sequence to be used to analyze multiple samples are introduced into the primer.

The tag sequence to be used is different from a sample to one another. For example, when preparing a 5-base tag sequences with four kinds of bases A, T, C, and G, $4^5=1024$ tag sequences are candidates. However, if tag sequences with a single base difference are used, the risk of mismatch hybridization increases. Hence, tag sequences with two or more base differences are preferably prepared. The tag sequences to be prepared need to be as many as the samples included in the sample group to be analyzed at once. This makes it possible to identify all samples included in the sample group.

The tag sequence is designed such that when a primer including it binds to a template nucleic acid, the tag sequence portion loops out without binding to the template nucleic acid. The tag sequence need only have a length in such a range that enables loop-out and allows the primer including the tag sequence to amplify the template nucleic acid. The tag sequence has, but is not limited to, a length of 20 bases or less, and preferably, 10 bases or less. For example, 1 to 20 bases, 2 to 20 bases, 1 to 10 bases, or 2 to 10 bases suffice.

The length of a primer may be 13 to 40 bases, for example, 15 to 30 bases.

The tag sequence insertion portion on the primer is located one or more bases apart from the 3'-end of the primer. However, since the primer needs to bind to the template while making the tag sequence portion loop out, the insertion portion is preferably located three or more bases apart from the 3'-end of the primer. As shown in FIG. 1, to detect a mutation or a polymorphism such as a single nucleotide polymorphism, the nucleic acid probe needs to include both the tag sequence and a sequence derived from the template sequence. In this case, if the insertion portion is located on the 5'-end side, the probe becomes longer, resulting in lower specificity. For this reason, the insertion portion is preferably close to the 3'-end as long as the primer can amplify the genes with loop-out. The insertion portion is located within the range of 25 bases and, more preferably, 15 bases from the 3'-end.

When PCR is used as the amplification method, the tag sequence-introduced primer to be used can be either a forward primer (F primer) or a reverse primer (R primer). The tag sequences may be introduced into both primers as needed.

When LAMP is used as the amplification method, a primer with the tag sequence introduced into the F2 region and/or the B2 region is prepared.

A substance such as DNA, RNA, PNA, LNA, S-oligo, or methyl phosphonate oligo is usable as the nucleic acid that forms the tag sequence, and the type of nucleic acid is not particularly limited if the partial structure can be expressed by a base sequence.

<Nucleic Acid Probe>

To detect the tag sequence included in a target nucleic acid, a nucleic acid probe is designed to include a sequence complementary to the tag sequence. As shown in FIG. 1, the nucleic acid probe is also designed to include a sequence complementary to the region derived from the template sequence, as needed.

For example, to detect a genetic mutation and/or polymorphism of the nucleic acid in the sample, the genetic mutation and/or genetic polymorphism portion is located in the region derived from the template sequence near the primer binding portion. Using a nucleic acid probe for detecting a wild type and a nucleic acid probe for detecting a mutation, each including a sequence for detecting a tag sequence and a sequence for detecting a genetic mutation and/or polymorphism, the amount of hybridization between the target nucleic acid and the nucleic acid probe for detecting a wild type is compared with that between the target nucleic acid and the nucleic acid probe for detecting a mutation, thereby determining the genotype of the sample.

To identify a plurality of species of organisms classified into the same genus, for example, the tag-introduced primer that commonly performs amplification for the genus is prepared for each sample to amplify the genes. At this time, a region that is characteristic to each species and can exhibit specificity to other species is located in the region derived from the template sequence near the primer binding portion. The amount of hybridization between the target nucleic acid and a nucleic acid probe for identifying a species, which has a sequence for detecting a tag sequence and a sequence characteristic to each species, is compared with that between the target nucleic acid and a negative control nucleic acid probe having a sequence irrelevant to the species, thereby identifying the species.

When detecting the presence/absence of amplification of the nucleic acid in the sample as an index for analysis, the sequence complementary to the region derived from the template sequence need not always be included. However, it may be included.

The strand length of the nucleic acid probe according to the embodiment is not particular limited, and preferably falls within the range of 5 to 50 bases, more preferably, within the range of 10 to 40 bases, and much more preferably, within the range of 15 to 35 bases.

The nucleic acid probe may be modified by a functional group such as an amino group, a carboxyl group, a hydroxyl group, a thiol group, or a sulfone group or a substance such as avidin or biotin for immobilization to the substrate. A spacer may be introduced between a nucleotide and the functional group. For example, an alkane backbone or an ethylene glycol backbone is usable as the spacer.

As the solid phase to immobilize the nucleic acid probe, any substrate generally used as a solid phase for a DNA chip is usable. The substrate can be made of glass, silicon, nitrocellulose membrane, nylon membrane, microtiter plate, electrode, magnet, bead, plastic, latex, synthetic resin, natural resin, or optical fiber. However, the present embodiment is not limited to those. A plurality of types of nucleic acid probes are immobilized on the substrate to form a DNA chip.

<Method>

A method of analyzing multiple samples using tag-introduced primers and a DNA chip will be described next.

As shown in FIG. 2, first, primers (primer for sample 1, primer for sample 2, and primer for sample 3) in which different tag sequences (tag sequence 1, tag sequence 2, and tag sequence 3) are introduced are prepared for the respective samples (sample 1, sample 2, and sample 3), and the genes are amplified in independent reaction systems for the respective samples. The independent reaction systems for the respective samples need only be reaction systems in which the samples do not mix. For example, amplification is done in separate tubes for the respective samples. The "reaction system" means a space where reaction occurs and can be a vessel such as a tube or a well.

After amplification, amplified products in which the sequence partially is different from a partial nucleic acid sequence to one another are obtained. If no template nucleic acid is present (sample 2), no amplification occurs, and no amplified product is obtained. The amplified products obtained in each reaction system include a tag sequence that is different from a sample to one another and a region derived from the template nucleic acid (sample 1 and sample 3). It is therefore possible to specify the sample by identifying the tag sequence included in the amplified product.

The amplified products are mixed and hybridized to the nucleic acid probes immobilized on the substrate and including sequences complementary to the tag sequences, as shown in FIG. 3. After that, the hybridization between each amplified product and a corresponding nucleic acid probe is detected by an appropriate detection method.

FIGS. 2 and 3 illustrate an example using three samples. However, the number of samples is obviously not limited to this. In addition, as shown in FIG. 1, when the primers are designed such that a mutation or a polymorphism is located in the region derived from the template sequence in the amplified product, the mutation and/or the polymorphism can be analyzed using a nucleic acid probe including the tag sequence and a sequence derived from the template sequence having a sequence for detecting or identifying the mutation and/or polymorphism.

Figure 4:
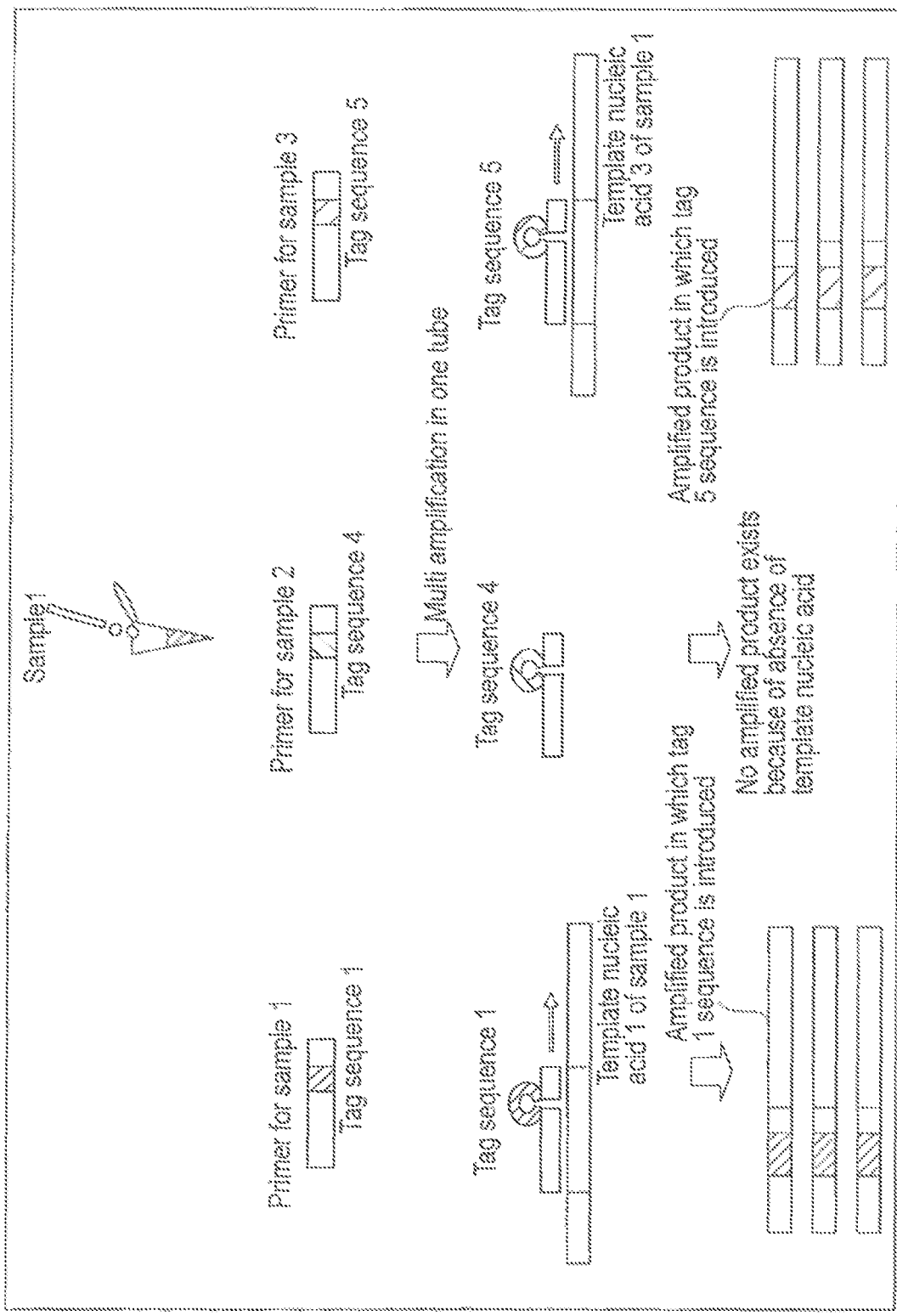
FIG. 4 is a scheme diagram showing an amplification step.

As shown in FIG. 4, a plurality of template sequences having different sequences may be multi-amplified in one reaction system. After amplification, DNA chip detection is performed for the amplified products of the sample, thereby detecting a plurality of template sequences. For detection, the amplified products are hybridized to nucleic acid probes immobilized on the substrate and including sequences complementary to the tag sequences. Then, the hybridization between each amplified product and a corresponding nucleic acid probe is detected by an appropriate detection method. FIG. 4 illustrates an example using three template sequences. However, the number of template nucleic acids is obviously not limited to this. In addition, when the primers are designed such that a mutation or a polymorphism and/or a portion that is characteristic to a biotic species to be identified and can exhibit specificity to other biotic species is located in the region derived from the template sequence in the amplified product, the mutation, polymorphism, or biotic species can be analyzed using a nucleic acid probe including the tag sequence and a sequence derived from the template sequence having a sequence for detecting or identifying the mutation, polymorphism, and/or a portion characteristic to the biotic species.

In the embodiment, the detection targets include, for example, genome DNA, genome RNA, and mRNA of an individual. The individuals include human, animals other than human, plants, and microorganisms such as viruses, bacteria, yeasts, and mycoplasmas.

The nucleic acids are extracted from a specimen collected from an individual such as blood, blood serum, white blood cells, urine, feces, sperm, saliva, tissue, biopsy, intraoral mucosa, cultured cells, or begma. Alternatively, the nucleic acids are directly extracted from a microorganism. Nucleic acid extraction can be executed using, for example, QIAamp (available from QIAGEN) or Smitest (available from Sumitomo Metals), which are commercially available nucleic acid extraction kits. A solution containing an individual specimen or a nucleic acid extracted from a micro-organism will be referred to as a test liquid.

The sample is amplified by an amplification method according to the embodiment. When the detection target is RNA, it can be converted into a complementary DNA strand using, for example, a reverse transcriptase before amplification. Both the reverse transcriptase and a DNA polymerase may be added into a single tube to simultaneously perform reverse transcription and amplification.

As the amplification method, for example, PCR (Polymerase Chain Reaction), LAMP (Loop Mediated Isothermal Amplification), ICAN (Isothermal and Chimeric primer-initiated Amplification of Nucleic acids), NASBA (Nucleic Acid Sequence-Based Amplification), SDA (Strand Displacement Amplification), LCR (Ligase Chain Reaction), or RCA (Rolling Circle Amplification) is usable. The obtained amplified product is fragmented or changed to a single strand, as needed. Single strand formation is done by, for example, thermal denaturation, a method using beads or an enzyme, or a method of causing transcription using T7 RNA polymerase. If an amplified product obtained by the LAMP or ICAN includes a single-stranded region to be used as the target sequence, the product can directly be used in the hybridization step.

The target nucleic acid obtained by amplification preferably has a stem loop structure because the single strand formation step is unnecessary. In the amplified product having the stem loop structure, the sequence of the single-stranded loop portion can conveniently be used for reaction with the probe.

To amplify a target nucleic acid, the LAMP (for example, see Japanese Patent No. 3313358) is suitably used. The LAMP is a quick and simple gene amplification method and forms an amplified product having the stem loop structure.

Figure 5:
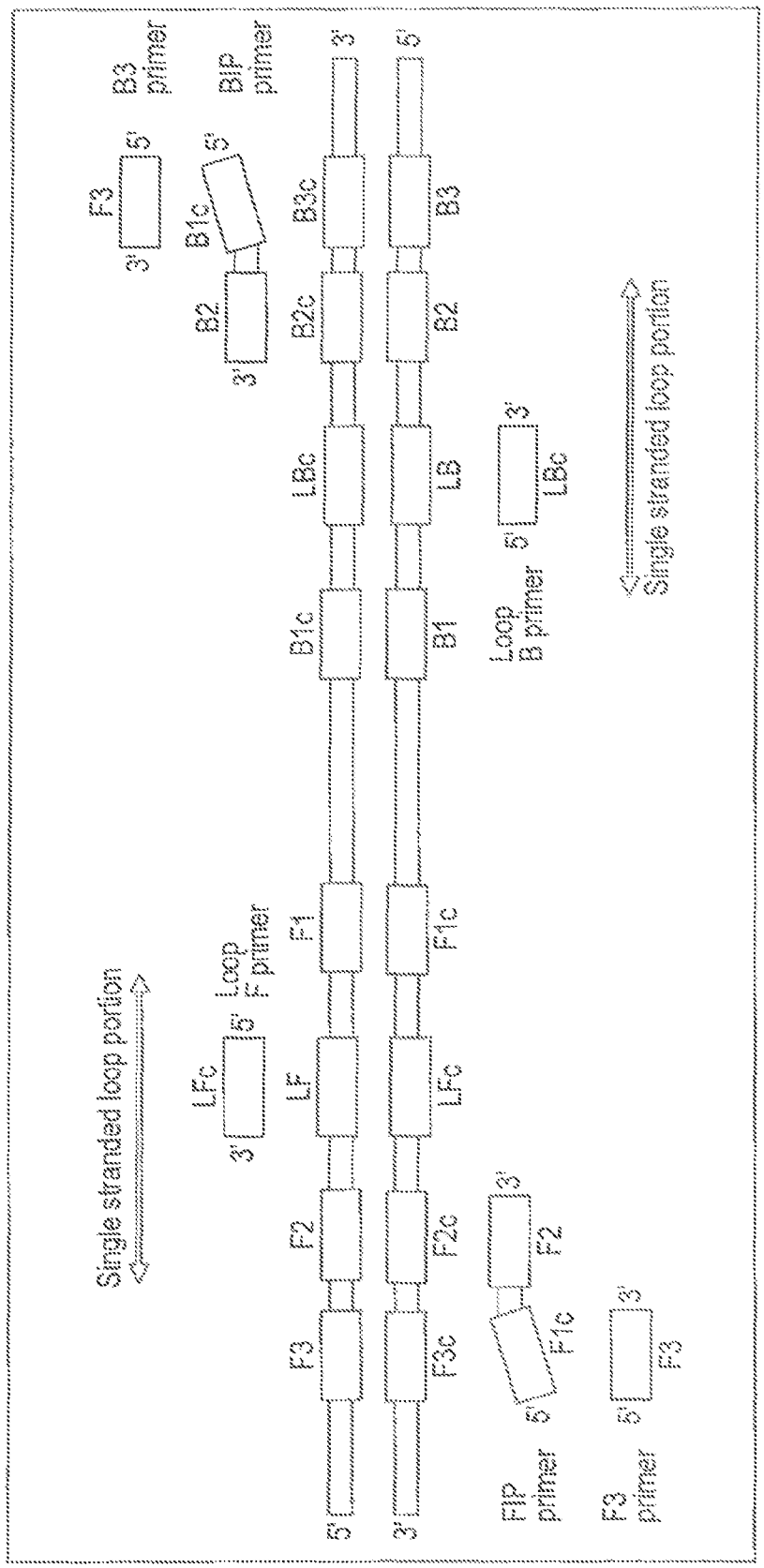
FIG. 5 is a view showing primers.

FIG. 5 is a view showing an example of basic primers used in the LAMP. The principle of the LAMP will briefly be explained with reference to the schematic view of FIG. 5. The LAMP uses a strand displacement type DNA synthetase and six different types of primers that recognize eight regions of the template nucleic acid at maximum. The template nucleic acid is amplified under an isothermal condition (60° C. to 65° C.). The eight regions are defined as an F3 region, an F2 region, an LF region, and an F1 region sequentially from the 5'-end side, and a B3c region, a B2c region, an LBc region, and a B1c region sequentially from the 3'-end side. Note that F1c, F2c, F3c, B1, B2, and B3 regions are regions in the complementary strand corresponding to the F1, F2, F3, B1c, B2c, and B3c regions. The eight types of primers shown in FIG. 5 are an FIP inner primer having a sequence complementary to F1 on the 5'-end side and the same sequence as F2 on the 3'-end side, a BIP inner primer having the same sequence as B1c on the 5'-end side and a sequence complementary to B2c on the 3'-end side, an F3 primer having the same sequence as the F3 region, a B3 primer having a sequence complementary to the B3c region, an LFc primer having a sequence complementary to the LF region, and an LBc primer having the same sequence as the LBc region. The FIP inner primer and the BIP inner primer are essential for the amplification reaction. The F3 primer, the B3 primer, the LF primer, and the LB primer are added to increase the amplification efficiency.

Figure 6:
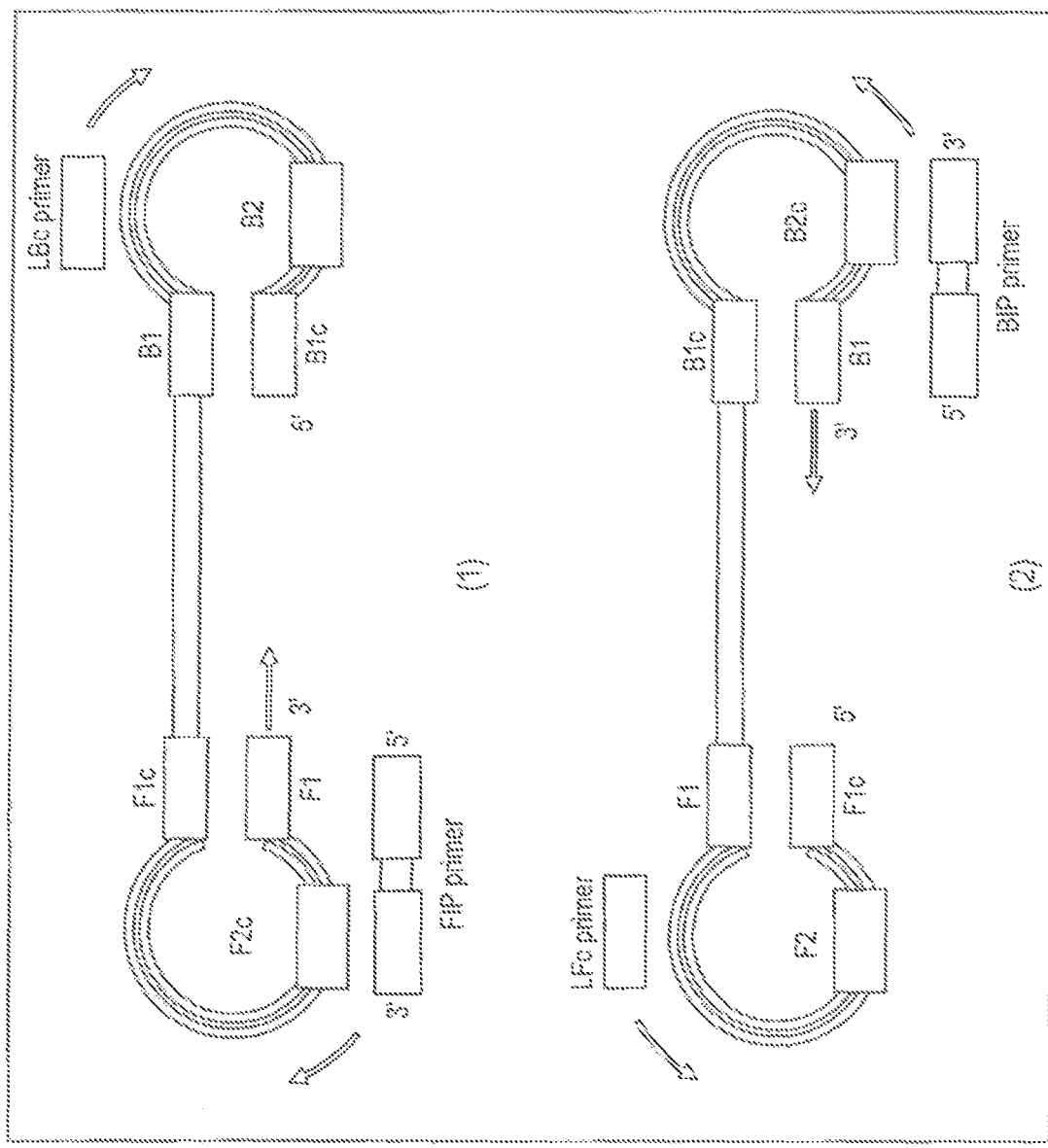
FIG. 6 is a view showing the intermediate product of LAMP amplification.

An amplified product obtained by the LAMP has a loop structure as shown in FIG. 6. Single-stranded regions are formed between the F2 region and the F1 region, between the F2c region and the F1c region, between the B2 region and the B1 region, and between the B2c region and the B1c region. Hence, designing the target sequence in these regions allows to simply and sensitively detect the target nucleic acid (for example, see Jpn. Pat. Appln. KOKAI Publication No. 2005-143492). If the target sequence overlaps the LF primer and/or the LB primer, it is preferable not to add the LF primer and/or the LB primer.

A method of analyzing multiple samples by the LAMP using tag-introduced primers and a DNA chip will be described with reference to FIG. 7.

First, primers in which the tag sequences are introduced in the F2 region and/or the B2 region are prepared for the respective samples.

Next, the genes are amplified for the respective samples in independent reaction systems for the respective samples. For example, amplification is done in separate tubes for the respective samples. After amplification, amplified products in which the sequence partially changes in the single-stranded loop portion depending on the sample are obtained. If no template nucleic acid is present, no amplification occurs, and no amplified product is obtained. The amplified products are mixed and hybridized to nucleic acid probes immobilized on the substrate and including sequences complementary to the tag sequences, as shown in FIG. 8. After that, the hybridization between each amplified product and a corresponding nucleic acid probe is detected by an appropriate detection method.

FIGS. 7 and 8 illustrate an example using three samples. However, the number of samples is obviously not limited to this.

As shown in FIG. 9, when a mutation or a polymorphism portion is located in a region derived from the template sequence detected by the nucleic acid probe, that is, between the F2 region and the F1 region, between the F2c region and the F1c region, between the B2 region and the B1 region, or between the B2c region and the B1c region, the mutation or the polymorphism can be detected using the nucleic acid probe for detecting the mutation or the polymorphism.

Figure 10:
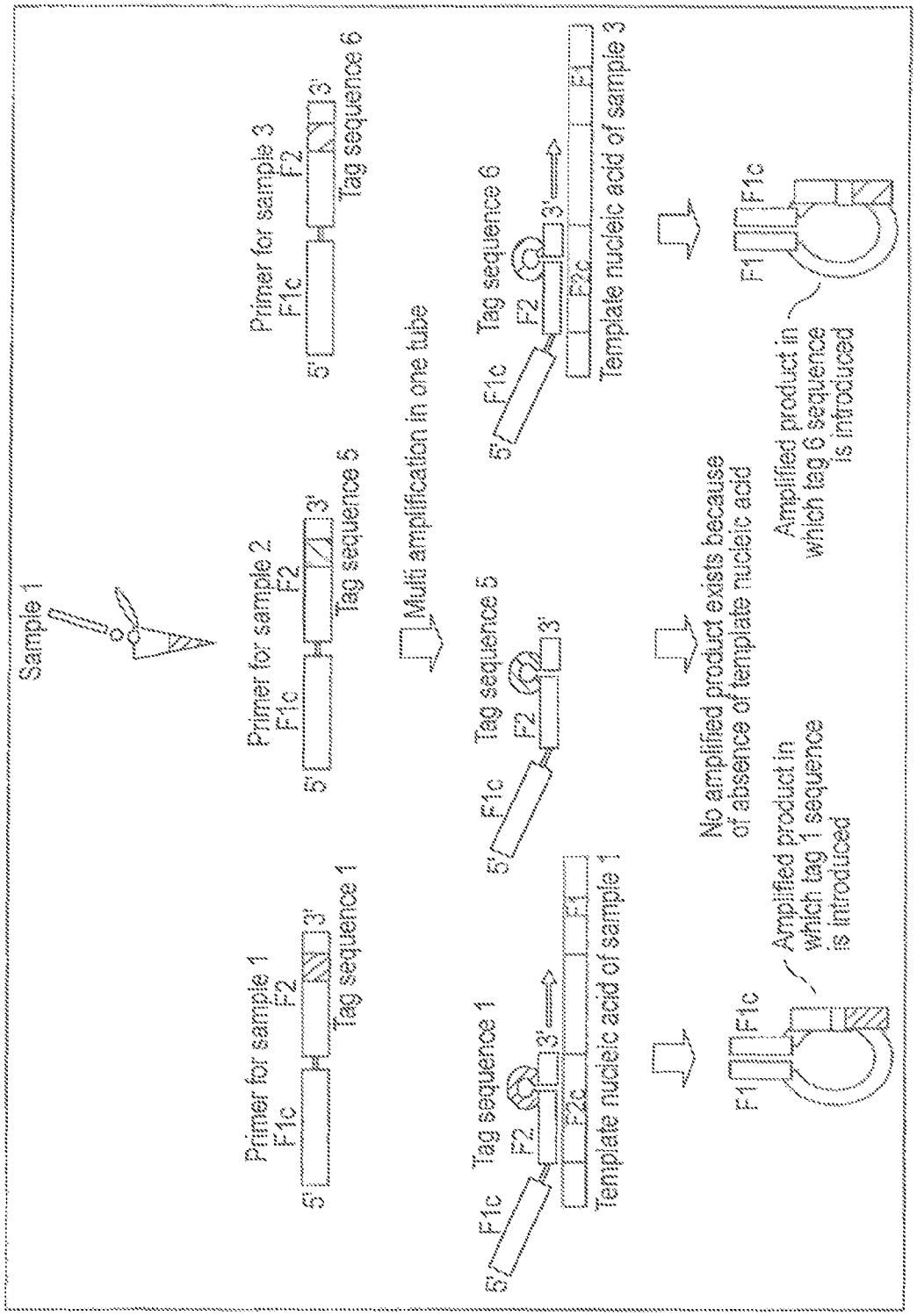
FIG. 10 is a scheme diagram showing an amplification step.

As shown in FIG. 10, a plurality of types of template sequences having different sequences may be multi-amplified in one reaction system. After amplification, DNA chip detection is performed for the amplified products of the sample, thereby analyzing plural samples for the plurality of target sequences. For detection, the amplified products are hybridized to nucleic acid probes immobilized on the substrate and including sequences complementary to the tag sequences. Then, the hybridization between each amplified product and a corresponding nucleic acid probe is detected by an appropriate detection method. FIG. 10 illustrates an example using three template nucleic acids. However, the number of template nucleic acids is obviously not limited to this. In addition, when the primers are designed such that a mutation or a polymorphism and/or a portion that is characteristic to a biotic species to be identified and can exhibit specificity to other biotic species is located in the region derived from the template sequence in the amplified product, the mutation, polymorphism, or biotic species can be analyzed using a nucleic acid probe including the tag sequence and a sequence derived from the template sequence having a sequence for detecting or identifying the mutation, polymorphism, and/or biotic species.

Since the method of the embodiment allows to test plural samples using one chip, there is provided a method of quickly and simply analyzing a plurality of samples at a lower test cost per sample.

<DNA Chip>

The DNA chip used in the embodiment need only comprise a substrate and a nucleic acid probe immobilized on the substrate. The substrate of the DNA chip can be a substrate for a microarray of any conventionally known type such as an electrochemical detection type represented by a current detection type, a fluorescence detection type, a chemical color development type, or a radioactivity detection type.

All types of microarrays can be manufactured by a method known by itself. For example, in a current detection type microarray, a negative control probe immobilization region and a detection probe immobilization region are arranged on different electrodes.

FIG. 11 is a schematic view showing an example of the DNA chip, though the embodiment is not limited to this. The DNA chip comprises immobilization regions 2 on a substrate 1. Nucleic acid probes are immobilized in the immobilization regions 2. Such a DNA chip can be manufactured by a method known in this field. Those skilled in the art can change the design concerning the number and arrangement of the immobilization regions 2 on the substrate 1 as needed. This DNA chip is suitably usable for a detection method using fluorescence.

FIG. 12 shows another example of the DNA chip. The DNA chip shown in FIG. 12 comprises electrodes 12 on a substrate 11. Nucleic acid probes are immobilized on the electrodes 12. Each electrode 12 is connected to a pad 13. Electrical information from the electrode 12 is acquired via the pad 13. Such a DNA chip can be manufactured by a method known in this field. Those skilled in the art can change the design concerning the number and arrangement of the electrodes 12 on the substrate 11 as needed. Additionally, the DNA chip of this example may comprise a reference electrode and a counter electrode as needed.

The electrodes can be made of a metal or an alloy thereof, for example, gold, gold alloy, silver, platinum, nickel, palladium, silicon, germanium, gallium, or tungsten, carbon such as graphite or glassy carbon or an oxide or compound thereof. However, the embodiment is not limited to those.

This DNA chip is suitably usable for an electrochemical detection method.

<Hybridization Conditions>

Hybridization is done under appropriate conditions where hybridization is sufficiently formed. The appropriate conditions change depending on the type and structure of the target nucleic acid, the types of bases included in the target sequence, and the type of the nucleic acid probe. For example, hybridization is performed in a buffer solution having an ionic strength of 0.01 to 5 and pH of 5 to 9. The reaction temperature can be 10° C. to 90° C. The reaction efficiency may be raised by agitation or shaking. The reaction solution may contain a hybridization accelerator such as dextran sulfate, salmon sperm DNA, or bovine thymus DNA, EDTA, or a surfactant.

<Washing Conditions>

As a wash to be used to wash the DNA chip after hybridization, a buffer solution having an ionic strength of 0.01 to 5 and pH of 5 to 9 is preferably used. The wash preferably contains salt, a surfactant, and the like. For example, SSC solution, Tris-HCl solution, Tween 20 solution, SDS solution, or the like prepared using sodium chloride or sodium citrate is suitably used. The washing temperature is 10° C. to 70° C. The wash passes through or builds up on the surface of the probe immobilization substrate or a region where a nucleic acid probe is immobilized. Alternatively, the DNA chip may be immersed in the wash. In this case, the wash is preferably stored in a vessel capable of controlling the temperature.

<Detection Method>

To detect a hybrid generated in the hybridization step, a fluorescence detection method and an electrochemical detection method are usable.

(a) Fluorescence Detection Method

A fluorescent labeling substance is used. The primers used in the nucleic acid amplification step may be labeled using a fluorescently active substance like a fluorescent dye such as FITC, Cy3, Cy5, or rhodamine. Alternatively, a second probe labeled by these substances may be used. A plurality of labeling substances may simultaneously be used. A detection apparatus detects the labeled sequence or the label in the second probe. An appropriate detection apparatus is used in accordance with the label to be used. For example, when a fluorescent substance is used as the label, a fluorescent detector is used for detection.

(b) Electrochemical Detection Method

A double strand recognition substance known in this field is used. The double strand recognition substance is selected from Hoechst 33258, acridine orange, quinacrine, daunomycin, metallointercalator, bisintercalator such as bisacridine, trisintercalator, and polyintercalator. These double strand recognition substances may be modified by an electrochemically active metal complex such as ferrocene or viologen.

The double strand recognition substance is generally used at a concentration of 1 ng/mL to 1 mg/mL although depending on the type. In this case, a buffer solution having an ionic strength of 0.001 to 5 and pH of 5 to 10 is usable.

Measurement is done by, for example, applying a potential equal to or higher than a potential at which the double strand recognition substance electrochemically reacts so as to measure the reaction current value derived from the double strand recognition substance. At this time, the potential can be applied at a constant speed or as pulses or a constant potential. The current and voltage may be controlled using a device such as a potentiostat, a digital multimeter, or a function generator. The electrochemical detection can be executed using a method known in this field. For example, a method described in Jpn. Pat. Appln. KOKAI Publication No. 10-146183 can be used.

<Assay Kit>

The embodiment also provides an assay kit to be used in the above-described nucleic acid analysis method. The assay kit comprises a primer set including a first primer including a tag sequence that has a sequence changing depending on a sample and is designed to loop out when hybridized to a template sequence in a template nucleic acid of each sample, and a second primer used in pair with the first primer; and a DNA chip including a substrate and a nucleic acid probe that is immobilized on the substrate and is complementary to a target sequence including the tag sequence.

At this time, the nucleic acid probe can be a nucleic acid probe that is complementary to a target sequence including the tag sequence and at least part of a sequence derived from the template sequence in the sample.

Alternatively, the assay kit comprises a primer set including a first primer including a tag sequence that has a sequence changing depending on a partial nucleic acid sequence and is designed to loop out when hybridized to a template sequence of each partial nucleic acid sequence, and the second primer used in pair with the first primer; and a DNA chip including a substrate and a nucleic acid probe that is immobilized on the substrate and is complementary to a target sequence including the tag sequence.

At this time, the nucleic acid probe can be a nucleic acid probe that is complementary to a target sequence including the tag sequence and at least part of a sequence derived from the template sequence of each partial nucleic acid sequence.

The first primer included in the assay kit includes primers whose types and amount are necessary for use in at least one analysis. To simultaneously analyze n samples, n types of first primers are used. When different types of first primers are compared in terms of the sequence, the sequences other than the tag sequences can be identical.

The second primer included in the assay kit includes primers whose amount is necessary for use in at least one analysis. Not only the first primer but also the second primer may also include a tag sequence. In this case, the second primer can include primers whose types and amount are necessary for use in at least one analysis. To simultaneously analyze n samples, n types of second primers are used. When different types of second primers are compared in terms of the sequence, the sequences other than the tag sequences can be identical.

If the assay kit uses PCR, the first primer includes, for example, n (n is an integer of 2 or more) type of forward primers or reverse primers including tag sequences associated with n samples that can include at least a template nucleic acid and a complementary sequence of a partial sequence of the template nucleic acid. The second primer includes primers whose amount is necessary for use in at least one analysis. Such a second primer is at least one type of reverse primer or forward primer to be used in pair with the first primer. When the first primer is a forward primer, the second primer is a reverse primer. When the first primer is a reverse primer, the second primer is a forward primer.

There is also provided an assay kit for an analysis method using LAMP. When the F3 region, the F2 region, the LF region, and the F1 region are designed from the 5'-end side of the template sequence, and the B3c region, the B2c region, the LBc region, and the B1c region from the 3'-end side, the assay kit includes at least one primer set selected from the group consisting of the following primer sets (1) to (9);

(1) an FIP primer (first primer) having a sequence complementary to F1 on the 5'-end side and the same sequence as F2 on the 3'-end side and including a tag sequence that is different from a sample to one another and is inserted in the F2 sequence, and a BIP primer (second primer) having the same sequence as B1c on the 5'-end side and a sequence complementary to B2c on the 3'-end side;

(2) an FIP primer (second primer) having a sequence complementary to F1 on the 5'-end side and the same sequence as F2 on the 3'-end side, and a BIP primer (first primer) having the same sequence as B1c on the 5'-end side and a sequence complementary to B2c on the 3'-end side and including a tag sequence that is different from a sample to one another and is inserted in the B2c sequence;

(3) an FIP primer (first primer) having a sequence complementary to F1 on the 5'-end side and the same sequence as F2 on the 3'-end side and including a tag sequence that is different from a sample to one another and is inserted in the F2 sequence, and a BIP primer (second primer) having the same sequence as B1c on the 5'-end side and a sequence complementary to B2c on the 3'-end side and including a tag sequence that is different from a sample to one another and is inserted in the B2c sequence;

(4) an FIP primer (first primer) having a sequence complementary to F1 on the 5'-end side and the same sequence as F2 on the 3'-end side and including a tag sequence that is different from a sample to one another and is inserted in the F2 sequence, a BIP primer (second primer) having the same sequence as B1c on the 5'-end side and a sequence complementary to B2c on the 3'-end side, an F3 primer (third primer) having the same sequence as the F3 region, and a B3 primer (fourth primer) having a sequence complementary to the B3c region;

(5) an FIP primer (second primer) having a sequence complementary to F1 on the 5'-end side and the same sequence as F2 on the 3'-end side, a BIP primer (first primer) having the same sequence as B1c on the 5'-end side and a sequence complementary to B2c on the 3'-end side and including a tag sequence that is different from a sample to one another and is inserted in the B2c sequence, an F3 primer (third primer) having the same sequence as the F3 region, and a B3 primer (fourth primer) having a sequence complementary to the B3c region;

(6) an FIP primer (first primer) having a sequence complementary to F1 on the 5'-end side and the same sequence as F2 on the 3'-end side and including a tag sequence that is different from a sample to one another and is inserted in the F2 sequence, a BIP primer (second primer) having the same sequence as B1c on the 5'-end side and a sequence complementary to B2c on the 3'-end side and including a tag sequence that is different from a sample to one another and is inserted in the B2c sequence, an F3 primer (third primer) having the same sequence as the F3 region, and a B3 primer (fourth primer) having a sequence complementary to the B3c region;

(7) an FIP primer (first primer) having a sequence complementary to F1 on the 5'-end side and the same sequence as F2 on the 3'-end side and including a tag sequence that is different from a sample to one another and is inserted in the F2 sequence, a BIP primer (second primer) having the same sequence as B1c on the 5'-end side and a sequence complementary to B2c on the 3'-end side, an F3 primer (third primer) having the same sequence as the F3 region, a B3 primer (fourth primer) having a sequence complementary to the B3c region, an LFc primer (fifth primer) having a sequence complementary to the LF region, and an LBc primer (sixth primer) having the same sequence as the LBc region;

(8) an FIP primer (second primer) having a sequence complementary to F1 on the 5'-end side and the same sequence as F2 on the 3'-end side, a BIP primer (first primer) having the same sequence as B1c on the 5'-end side and a sequence complementary to B2c on the 3'-end side and including a tag sequence that is different from a sample to one another and is inserted in the B2c sequence, an F3 primer (third primer) having the same sequence as the F3 region, a B3 primer (fourth primer) having a sequence complementary to the B3c region, an LFc primer (fifth primer) having a sequence complementary to the LF region, and an LBc primer (sixth primer) having the same sequence as the LBc region; and (9) an FIP primer (first primer) having a sequence complementary to F1 on the 5'-end side and the same sequence as F2 on the 3'-end side and including a tag sequence that is different from a sample to one another and is inserted in the F2 sequence, a BIP primer (second primer) having the same sequence as B1c on the 5'-end side and a sequence complementary to B2c on the 3'-end side and including a tag sequence that is different from a sample to one another and is inserted in the B2c sequence, an F3 primer (third primer) having the same sequence as the F3 region, a B3 primer (fourth primer) having a sequence complementary to the B3c region, an LFc primer (fifth primer) having a sequence complementary to the LF region, and an LBc primer (sixth primer) having the same sequence as the LBc region.

The assay kit may also include an enzyme to be used to cause an amplification reaction and/or a vessel, a wash, a buffer solution, a salt to be used to prepare the buffer solution, and the like. The DNA chip may include the nucleic acid probe and the substrate in an unintegrated state.

Such an assay kit enables to more simply analyze a nucleic acid.

EXAMPLES

Detailed examples of detection by the method according to the embodiment will be described. In the following examples, plural samples are analyzed using a DNA chip and primers in which a tag sequence changing depending on the sample is inserted.

(1) Amplification of Template Nucleic Acid

First, gene amplification was done using primers with tag sequences inserted. It was confirmed using a restriction enzyme whether a target genetic product was generated. A human MTHFR gene of SEQ ID NO: 21 was used as the template nucleic acid and amplified by the LAMP.

<Primers>

Table 1 shows synthetic DNA oligo primers used to amplify the target nucleic acid.

A total of 11 types of FIP primers, that is, an FIP primer (FIP-1; SEQ ID NO: 1) without inserted base, FIP primer (FIP-2; SEQ ID NO: 2) with AC inserted to the fourth base from the 3'-end side, FIP primer (FIP-3; SEQ ID NO: 3) with ACAC inserted, FIP primer (FIP-4; SEQ ID NO: 4) with ACACAC inserted, FIP primer (FIP-5; SEQ ID NO: 5) with TGTG inserted, FIP primer (FIP-6; SEQ ID NO: 6) with TCTC inserted, FIP primer (FIP-7; SEQ ID NO: 7) with AC inserted to the sixth base from the 3'-end side, FIP primer (FIP-8; SEQ ID NO: 8) with ACAC inserted, FIP primer (FIP-9; SEQ ID NO: 9) with ACACAC inserted, FIP primer (FIP-10; SEQ ID NO: 10) with TGTG inserted, and FIP primer (FIP-11; SEQ ID NO: 11) with TCTC inserted were prepared. A BIP printer (SEQ ID NO: 12), F3 primer (SEQ ID NO: 13), B3 primer (SEQ ID NO: 14), and LBc primer (SEQ ID NO: 15) were commonly used.

TABLE 1

| Primer | Sequence |
|---|---|
| FIP-1 | GGAAGAATGTGTCAGCCTCAAAG(F1c)-TGAAGGAGAAGGTGTCTGCGG(F2) |
| FIP-2 | GGAAGAATGTGTCAGCCTCAAAG(F1c)-TGAAGGAGAAGGTGTCTACGCGG(F2) |

TABLE 1-continued

| Primer | Sequence |
|---|---|
| FIP-3 | GGAAGAATGTGTCAGCCTCAAAG(F1c)-TGAAGGAGAAGGTGTCTACACGCGG(F2) |
| FIP-4 | GGAAGAATGTGTCAGCCTCAAAG(F1c)-TGAAGGAGAAGGTGTCTACACACGCGG(F2) |
| FIP-5 | GGAAGAATGTGTCAGCCTCAAAG(F1c)-TGAAGGAGAAGGTGTCTTGTGGCGG(F2) |
| FIP-6 | GGAAGAATGTGTCAGCCTCAAAG(F1c)-TGAAGGAGAAGGTGTCTTCTCGCGG(F2) |
| FIP-7 | GGAAGAATGTGTCAGCCTCAAAG(F1c)-TGAAGGAGAAGGTGTACCTGCGG(F2) |
| FIP-8 | GGAAGAATGTGTCAGCCTCAAAG(F1c)-TGAAGGAGAAGGTGTACACCTGCGG(F2) |
| FIP-9 | GGAAGAATGTGTCAGCCTCAAAG(F1c)-TGAAGGAGAAGGTGTACACACCTGCGG(F2) |
| FIP-10 | GGAAGAATGTGTCAGCCTCAAAG(F1c)-TGAAGGAGAAGGTGTTGTGCTGCGG(F2) |
| FIP-11 | GGAAGAATGTGTCAGCCTCAAAG(F1c)-TGAAGGAGAAGGTGTTCTCCTGCGG(F2) |
| BIP | CAGGAGAGCCCATAAGCTCCCT(B1c)-TCAGCACTCCACCCAGAG(B2) |
| F3 | GTTACCCCAAAGGCCACC |
| B3 | TCTGGGAAGAACTCAGCGAA |
| LBc | CCGCACCGTCCTCGCACAGGC |

Primers FIP-1 to FIP-11 correspond to SEQ ID NO NOs: 1-11, respectively. BIP, F3, B3 and LBc corresponds to SEQ IS NOs: 12-15, respectively.

<LAMP Reaction Liquid>

Table 2 shows the composition of the reaction solution used in the LAMP.

TABLE 2

| Bst DNA Polymerase | 2 µL |
|---|---|
| 2×Buffer | 12.5 µL |
| Tris•HCl pH8.0 40 mM | |
| KCl 20 mM | |
| MgSO$_4$ 16 mM | |
| (NH$_4$)$_2$SO$_4$ 20 mM | |
| Tween20 0.2% | |
| Betaine 1.6M | |
| dNTP 2.8 mM | |
| F3 primer (20 µM) | 0.5 µL |
| B3 primer (20 µM) | 0.5 µL |
| FIP primer (40 µM) | 2 µL |
| BIP primer (40 µM) | 2 µL |
| LFc primer (20 µM) | 2 µL |
| Human genome (60 ng/µL) | 1 µL |
| Sterilized ultrapure water | 2.5 µL |
| Total | 25 µL |

<Nucleic Acid Amplification>

The nucleic acid was amplified by the LAMP at 63° C. for 1 hr. In the negative control, sterilized water was used in place of the template nucleic acid. The rise time of amplification was measured by detecting the turbidity of pyrophosphate generated in accordance with the amplification reaction and magnesium in the solution using a Loopamp real-time turbidimeter.

<Target Product Confirmation Using Restriction Enzymes>

The FIP primers with AC (FIP-2), ACAC (FIP-3), and ACACAC (FIP-4) introduced to the fourth base from the 3'-end side were broken by AccI. The FIP primer (FIP-1) without inserted base is not broken by AccI. However, in the primers with AC (FIP-2), ACAC (FIP-3), and ACACAC (FIP-4) inserted, the inserted portion of the primer loops out and anneals to the template nucleic acid. Hence, when the target product has been generated, the amplified product is broken by AccI.

Similarly, the FIP primers with AC (FIP-7), ACAC (FIP-8), and ACACAC (FIP-9) inserted to the sixth base from the 3'-end side were broken by CviQl. The FIP primer (FIP-1) without inserted base is not broken by CviQl. In the primers with AC (FIP-7), ACAC (FIP-8), and ACACAC (FIP-9) inserted, the inserted portion of the primer loops out and anneals to the template nucleic acid. Hence, when the target product has been generated, the amplified product is broken by CviQl.

<Result>

The rise time for the primer (FIP-1) without inserted base was 29 min. The rise times for the specimens of the primers with AC (FIP-2), ACAC (FIP-3), ACACAC (FIP-4), TGTG (FIP-5), and TCTC (FIP-6) inserted to the fourth base from the 3'-end side were 32 min, 37 min, 38 min, 38 min, and 37 min, respectively. The rise times for the specimens of the primers with AC (FIP-7), ACAC (FIP-8), ACACAC (FIP-9), TGTG (FIP-10), and TCTC (FIP-11) inserted to the sixth base from the 3'-end side were 30 min, 38 min, 47 min, 32 min, and 35 min, respectively. In the negative control, the amplification did not rise. This revealed that base insertion allowed the amplification to rise within 50 min without any problem to obtain an amplified product. In addition, it was confirmed using the restriction enzymes that the target product was amplified, as shown in FIG. 13.

(2) DNA Chip Detection of Target Nucleic Acid

Amplification was done using the FIP primers with ACAC (FIP-3), TGTG (FIP-5), TCTC (FIP-6) inserted to the fourth base from the 3'-end side. The B3, F3, BIP, and LBc primers were commonly used (see Table 1). Two types of templates were prepared by adding human genome and sterilized water in place of the human genome. After that, chip detection was performed for the obtained amplified products.

<Nucleic Acid Probes>

Table 3 shows synthetic DNA oligo nucleic acid probes used for detection. In this example, as the nucleic acid probes, FIP primer (probe 2; SEQ ID NO: 17) with ACAC inserted to the fourth base from the 3'-end side, FIP primer (probe 3; SEQ ID NO: 18) with TGTG inserted, FIP primer (probe 4; SEQ ID NO: 19) with TCTC inserted, and FIP primer (probe 5; SEQ ID NO: 20) with one base mutation inserted to the prospective complementary strand portion of the region derived from the template sequence were prepared. As the negative control, a negative probe (probe 1; SEQ ID NO: 16) having a sequence irrelevant to the MTHFR genetic sequence was used. The 3'-end sides of these five types of probes were modified by thiol so as to be immobilized to gold electrodes.

TABLE 3

| Probe | Sequence |
| --- | --- |
| 1 | GTGCTGCAGGTGCG |
| 2 | CTACACGCGGGAGCCGAT |
| 3 | CTTGTGGCGGGAGCCGAT |
| 4 | CTTCTCGCGGGAGCCGAT |
| 5 | CTACACGCGGGAGGCGAT |

Probes 1-5 correspond to SEQ ID NO: 16-20.

<Electrochemical Detection DNA Chip>

The above-described nucleic acid probes were immobilized to the gold electrodes. Immobilization of the nucleic acid probes was done using the strong covalency between thiol and gold. A nucleic acid probe solution was spotted on the gold electrodes and left at rest at 25° C. for 1 hr. After that, the substrate was immersed in a 1-mM mercaptohexnol solution and washed by a 0.2×SSC solution. Identical probes of each type were spotted on four electrodes. The positions of the electrodes of the nucleic acid probes are as follows. After washing, the substrate was washed by ultrapure water and air-dried, thereby obtaining an electrochemical detection DNA chip.

<Electrode Arrangement>

The correspondence between the electrodes and the nucleic acid probes immobilized thereon is as follows.

1-4 electrodes negative probe (nucleic acid probe 1)

5-8 electrodes ACAC detection probe (nucleic acid probe 2)

9-12 electrodes TGTG detection probe (nucleic acid probe 3)

13-16 electrodes TCTC detection probe (nucleic acid probe 4)

17-20 electrodes ACAC one base mutation introduced probe (nucleic acid probe 5)

<Hybridization>

The thus prepared electrochemical detection DNA chip was immersed in a LAMP product with 2×SSC salt added and left at rest at 55° C. for 10 min to cause hybridization. After that, the electrochemical detection DNA chip was immersed in the 0.2×SSC solution at 48° C. for 10 min and washed. Next, the electrochemical detection DNA chip was immersed in a phosphate buffer solution containing 50-µM Hoechst 33258 solution serving as an intercalating agent for 1 min. Then, the oxidation current response of the Hoechst 33258 solution was measured.

<Result>

Figure 14B:
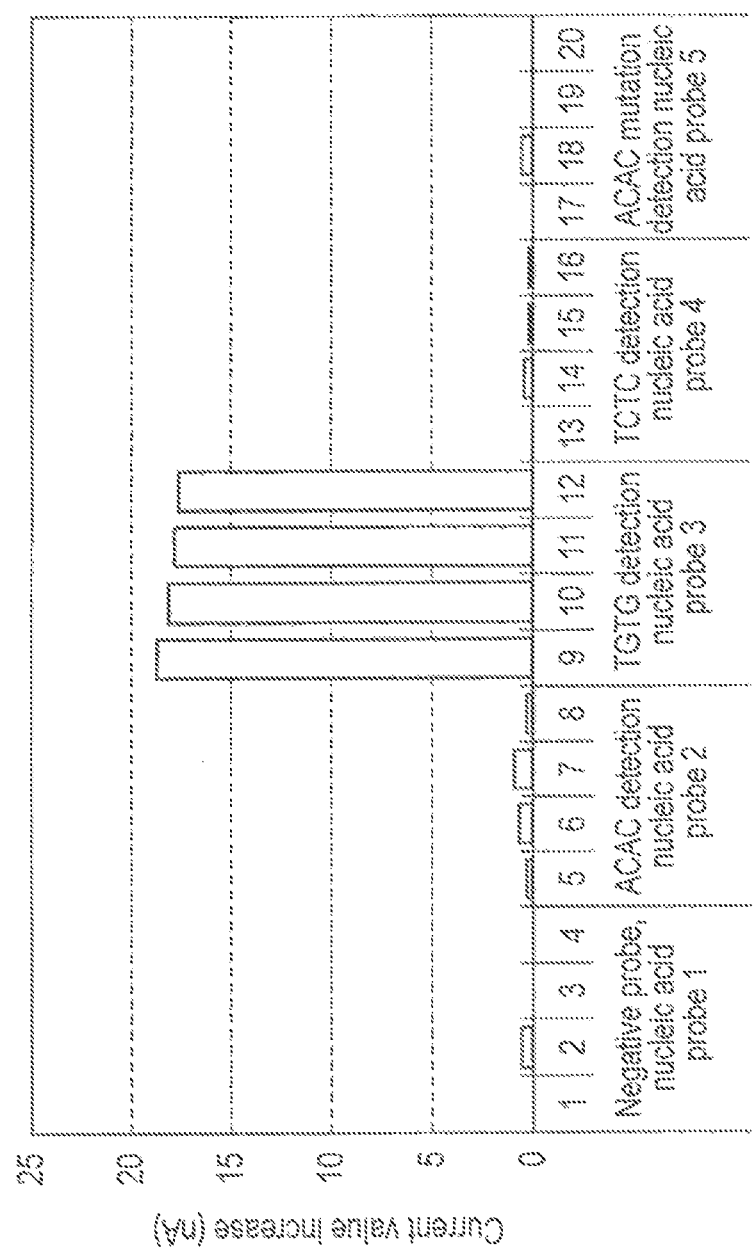
FIG. 14B is a graph showing a result of detection of plural samples.
Figure 14C:
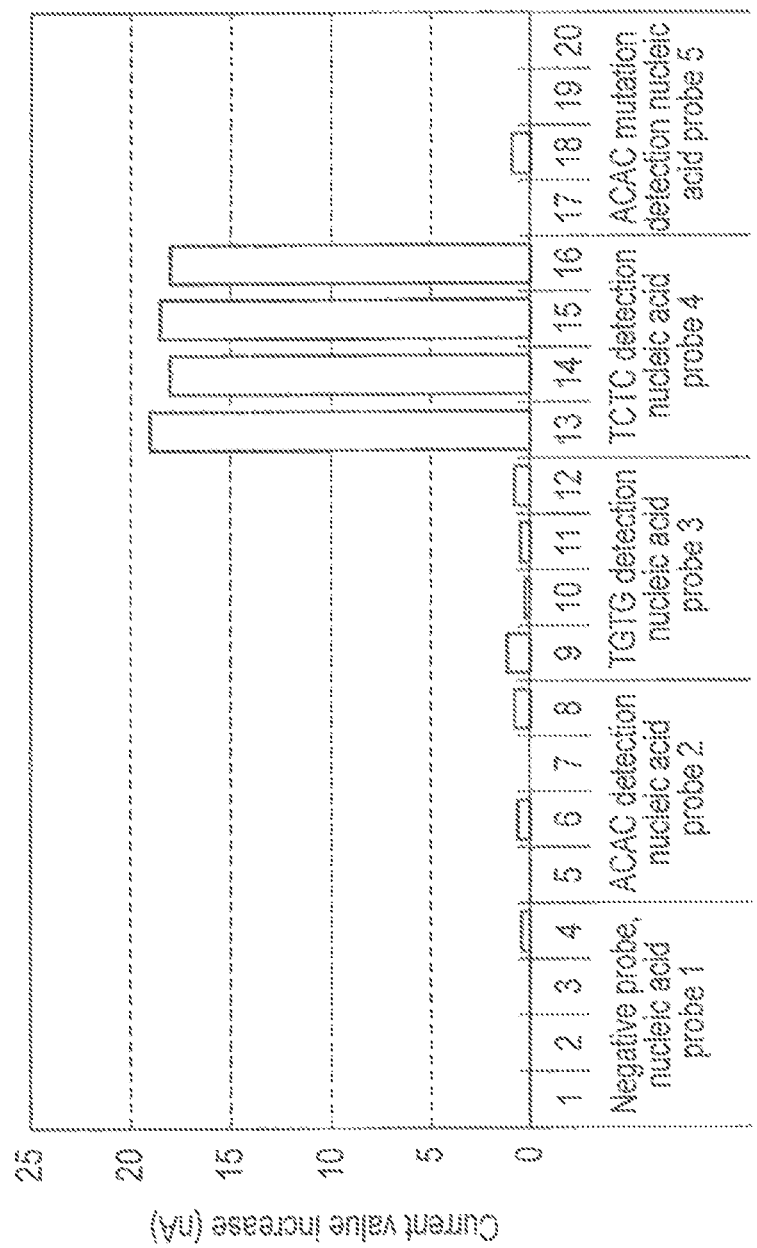
FIG. 14C is a graph showing a result of detection of plural samples.

FIG. 14A shows the mixture of the amplified product of the primer set with ACAC (FIP-3) inserted, which was obtained by adding human genome and performing amplification, and the amplified product of the primer set with TGTG (FIP-5) and TCTC (FIP-6) inserted, which was obtained by adding sterilized water and performing amplification. FIG. 14B shows the mixture of the amplified product of the primer set with TGTG (FIP-5) inserted, which was obtained by adding human genome and performing amplification, and the amplified product of the primer set with ACAC (FIP-3) and TCTC (FIP-6) inserted, which was obtained by adding sterilized water and performing amplification. FIG. 14C shows the mixture of the amplified product of the primer set with TCTC (FIP-6) inserted, which was obtained by adding human genome and performing amplification, and the amplified product of the primer set with ACAC (FIP-3) and TGTG (FIP-5) inserted, which was obtained by adding sterilized water and performing amplification. As the result of chip detection, a high signal was obtained from nucleic acid probe 2 for detecting ACAC in FIG. 14A. In FIG. 14B, a high signal was obtained from nucleic acid probe 3 for detecting TGTG. In FIG. 14C, a high signal was obtained from nucleic acid probe 4 for detecting TCTC. This revealed that the tag-inserted primer of the embodiment allowed to simultaneously detect plural samples using a DNA chip. Additionally, in FIG. 14A, the signal of nucleic acid probe 5 different from ACAC detection probe in one base lowered as compared to nucleic acid probe 2 under a stricter washing condition. This suggested that locating a mutation in the region derived from the template sequence allowed to detect the mutation.

In this example, three samples were simultaneously detected. However, the number of samples is obviously not limited to this. The number of samples can be changed as needed. The tag sequence insertion position and the number of bases are obviously not limited to those described above, either. They can be changed as needed.

As described in the example, the plural samples were easily and simply analyzed in a short time by the analysis method of the embodiment.

The embodiment is useful for analyzing nucleic acids such as genes in the fields of medical care, medicine, food, agriculture, fishery, animal husbandry, gardening, and the like.

REFERENCE SIGNS LIST

1 ... substrate

2 ... immobilization region

11 ... substrate

12 ... electrode

13 ... pad

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method of analyzing plural samples, wherein each of the plural samples comprises a template sequence to be amplified by a primer set, the method comprising the steps of:

(a) preparing, for each sample, the primer set comprising a first primer and second primer, wherein the first primer comprises a first sequence, a second sequence and a tag sequence being at between the first sequence and the second sequence, the first sequence having a sequence complementary to a first part of the template sequence, the second sequence having a sequence complementary to a second part located adjacent to the first part on the template nucleic acid, wherein each tag has a sequence different from any other tag sequence, and the tag sequences are different from a complementary sequence of the sample wherein the tag sequence is designed such that when a primer comprising the tag is bound to a template nucleic acid, the tag sequence portion loops out without binding to the template nucleic acid; and wherein the second primer is a primer for use to amplify the template sequence in pair with the first primer;

(b) amplifying the template nucleic acid of each sample using the primer set corresponding to each of the samples in an independent reaction system to obtain amplified products comprising the first sequence, the second sequence and the tag sequence respectively;

(c) mixing the amplified products obtained for the respective samples to obtain a single mixture of amplified products obtained in all of the independent reaction systems of (b);

(d) bringing the mixture of (c) into a reaction with a plurality of nucleic acid probes, wherein each of the nucleic acid probe has a sequence complementary to a target sequence which comprises the tag sequence, and a sequence derived from the template sequence for each of the plurality of sample, wherein the nucleic acid probes are immobilized on a substrate; and (e) detecting an amount of hybridization that has occurred in the step (d) so as to detect the presence or absence and/or an amount of the target nucleic acid for each of the plural samples.

2. The method according to claim 1, wherein the amplifying by the primer set is LAMP amplification, wherein the template nucleic acid includes an F3 region, an F2 region, an LF region and an F1 region from 5'-end side of the template nucleic acid in the order, and a B3c region, a B2c region, an LBc region, and a B1c region from a 3'-end side of the template nucleic acid in the order, wherein the F3 region has a F3 sequence, the F2 region has a F2 sequence, the LF region has a LF sequence, the F1 region has a F1 sequence, the B3c region has a B3c sequence, the B2c region has a B2c sequence, the LBc region has a LBc sequence and B1c region has a B1c sequence, wherein at least one primer set is selected from the group consisting of:

(1) a primer set comprising an FIP primer which is the first primer and a BIP primer which is the second primer, the FIP primer having a sequence complementary to F1 on the 5'-end side and a same sequence as the F2 sequence on the 3'-end side and the tag sequence inserted in the same sequence as the F2 sequence, and the BIP primer having the same sequence as the B1c sequence on the 5'-end side and a sequence complementary to B2c on the 3'-end side;

(2) a primer set comprising an FIP primer which is the second primer and a BIP primer which is the first primer, the FIP primer having a sequence complementary to the F1 sequence on the 5'-end side and a same sequence as the F2 sequence on the 3'-end side, and the BIP primer having a same sequence as the B1c sequence on the 5'-end side and a sequence complementary to the B2c sequence on the 3'-end side and the tag sequence inserted in the sequence complementary to the B2c sequence;

(3) a primer set comprising an FIP primer which is the first primer and a BIP primer which is the second primer, the FIP primer having a sequence complementary to F1 on the 5'-end side and a same sequence as the F2 sequence on the 3'-end side and the tag sequence inserted in the same sequence as the F2 sequence, and the BIP primer having a same sequence as B1c on the 5'-end side and a sequence complementary to the B2c sequence on the 3'-end side and the tag sequence inserted in the sequence complementary to the B2c sequence;

(4) a primer set comprising an FIP primer which is the first primer and a BIP primer which is the second primer, an F3 primer and a B3 primer, the FIP primer having a sequence complementary to F1 on the 5'-end side and a same sequence as the F2 sequence on the 3'-end side and the tag sequence inserted in the same sequence as the F2 sequence, the BIP primer having a same sequence as the B1c sequence on the 5'-end side and a sequence complementary to the B2c sequence on the 3'-end side, the F3 primer having a same sequence as the F3 sequence, and the B3 primer having a sequence complementary to the B3c sequence;

(5) a primer set comprising an FIP primer which is the second primer and a BIP primer which is the first primer, an F3 primer and a B3 primer, the FIP primer having a sequence complementary to F1 on the 5'-end side and a same sequence as the F2 sequence on the 3'-end side, the BIP primer having a same sequence as the B1c sequence on the 5'-end side and a sequence complementary to the B2c sequence on the 3'-end side and the tag sequence inserted in the sequence complementary to the B2c sequence, the F3 primer having a same sequence as the F3 sequence, and the B3 primer having a sequence complementary to the B3c region;

(6) a primer set comprising an FIP primer which is the first primer and a BIP primer which is the second primer, an F3 primer and a B3 primer, the FIP primer having a sequence complementary to F1 on the 5'-end side and a same sequence as the F2 sequence on the 3'-end side and the tag sequence inserted in the same sequence as the F2 sequence, the BIP primer having a same sequence as the B1c sequence on the 5'-end side and a sequence complementary to the B2c sequence on the 3'-end side and the tag sequence inserted in the sequence complementary to the B2c sequence, an F3 primer having a same sequence as the F3 sequence, and a B3 primer having a sequence complementary to the B3c sequence;

(7) a primer set comprising an FIP primer which is the first primer and a BIP primer which is the second primer, an F3 primer, a B3 primer, an LFc primer and an LBc primer, the FIP primer having a sequence complementary to the F1 sequence on the 5'-end side and a same sequence as the F2 sequence on the 3'-end side and the tag sequence inserted in the same sequence as the F2 sequence, the BIP primer having a same sequence as the B1c sequence on the 5'-end side and a sequence complementary to the B2c sequence on the 3'-end side, the F3 primer having a same sequence as the F3 sequence and the B3 primer having a sequence complementary to the B3c sequence, and the LFc primer having a sequence complementary to the LF sequence, and/or the LBc primer having a same sequence as the LBc sequence;

(8) a primer set comprising an FIP primer which is the second primer and a BIP primer which is the first primer, an F3 primer, a B3 primer, an LFc primer and an LBc primer, the FIP primer having a sequence complementary to the F1 sequence on the 5'-end side and a same sequence as the F2 sequence on the 3'-end side, the BIP primer having a same sequence as the B1c sequence on the 5'-end side and a sequence complementary to the B2c sequence on the 3'-end side and the tag sequence inserted in the sequence complementary to the B2c sequence, the F3 primer having a same sequence as the F3 sequence and the B3 primer having a sequence complementary to the B3c sequence, and the LFc primer having a sequence complementary to the LF sequence, and/or the LBc primer having a same sequence as the LBc sequence; and (9) a primer set comprising an FIP primer which is the first primer and a BIP primer which is the second primer, an F3 primer, a B3 primer, an LFc primer and an LBc primer, the FIP primer having a sequence complementary to F1 on the 5'-end side and a same sequence as the F2 sequence on the 3'-end side and the tag sequence inserted in the same sequence as the F2 sequence, the BIP primer having a same sequence as the B1c sequence on the 5'-end side and a sequence complementary to the B2c sequence on the 3'-end side and the tag sequence inserted in the sequence complementary to the B2c sequence, the F3 primer having a same sequence as the F3 sequence and the B3 primer having a sequence complementary to the B3c sequence, and the LFc primer having a sequence complementary to the LF sequence, and/or the LBc primer having a same sequence as the LBc sequence.

3. A method of analyzing a plurality of partial nucleic acid sequences in a sample nucleic acid, the sample nucleic acid comprising a plurality of template sequences for the partial nucleic acid sequences, to be amplified by a primer set, the method comprising the steps of:

(a) preparing, for each partial nucleic acid sequence, the primer set comprising a first primer and second primer, wherein the first primer includes a first sequence, a second sequence and a tag sequence being at between the first sequence and the second sequence, the first sequence having a sequence complementary to a first part on the template sequence and the second sequence having a sequence complementary to a second part located adjacent to the first part on the template nucleic acid, wherein each tag has a sequence different from any other tag sequence, and the tag sequences are different from a complementary sequence of the sample wherein the tag sequence is designed such that when a primer comprising the tag is bound to a template nucleic acid, the tag sequence portion loops out without binding to the template nucleic acid; and wherein the second primer is a primer for use to amplify each of the plurality of template sequence;

(b) amplifying all of the template sequences in one reaction system using the primer sets to obtain an amplified products mixture, each amplified product including the first sequence, the second sequence and the tag sequence of the first primer;

(c) bringing the amplified products mixture of (b) into a reaction with a plurality of nucleic acid probes, wherein each of the nucleic acid probes have a sequence complementary to a target sequence which comprises the tag sequence, and a sequence derived from the template sequence for each of the plurality of partial nucleic acid sequences, and wherein the nucleic acid probes are immobilized on a substrate; and (d) detecting an amount of hybridization that has occurred in the step (c) so as to detect the presence or absence and/or an amount of the target nucleic acid for each partial nucleic acid sequence.

4. The analysis method according to claim 3, wherein the amplifying by the primer set is LAMP amplification, wherein the template nucleic acid includes an F3 region, an F2 region, an LF region and an F1 region from 5'-end side of the template nucleic acid in the order, and a B3c region, a B2c region, an LBc region, and a B1c region from a 3'-end side of the template nucleic acid in the order, wherein the F3 region has a F3 sequence, the F2 region has a F2 sequence, the LF region has a LF sequence, the F1 region has a F1 sequence, the B3c region has a B3c sequence, the B2c region has a B2c sequence, the LBc region has a LBc sequence and B1c region has a B1c sequence, wherein at least one primer set is selected from the group consisting of:

(1) a primer set comprising an FIP primer which is the first primer and a BIP primer which is the second primer, the FIP primer having a sequence complementary to F1 on the 5'-end side and a same sequence as the F2 sequence on the 3'-end side and the tag sequence inserted in the same sequence as the F2 sequence, and the BIP primer having a same sequence as the B1c sequence on the 5'-end side and a sequence complementary to the B2c sequence on the 3'-end side;

(2) a primer set comprising an FIP primer which is the second primer and a BIP primer which is the first primer, the FIP primer having a sequence complementary to the F1 sequence on the 5'-end side and a same sequence as the F2 sequence on the 3'-end side, and the BIP primer having a same sequence as the B1c sequence on the 5'-end side and a sequence complementary to the B2c sequence on the 3'-end side and the tag sequence inserted in the sequence complementary to the B2c sequence;

(3) an FIP primer having a sequence complementary to the F1 sequence on the 5'-end side and a same sequence as the F2 sequence on the 3'-end side and the tag sequence inserted in the same sequence as the F2 sequence, and a BIP primer having a same sequence as the B1c sequence on the 5'-end side and a sequence complementary to the B2c sequence on the 3'-end side and the tag sequence inserted in the sequence complementary to the B2c sequence;

(4) an FIP primer having a sequence complementary to the F1 sequence on the 5'-end side and a same sequence as the F2 sequence on the 3'-end side and the tag sequence inserted in the same sequence as the F2 sequence, a BIP primer having a same sequence as the B1c sequence on the 5'-end side and a sequence complementary to the B2c sequence on the 3'-end side, an F3 primer having a same sequence as the F3 sequence, and a B3 primer having a sequence complementary to the B3c sequence;

(5) an FIP primer having a sequence complementary to F1 on the 5'-end side and a same sequence as the F2 sequence on the 3'-end side, a BIP primer having a same sequence as the B1c sequence on the 5'-end side and a sequence complementary to the B2c sequence on the 3'-end side and the tag sequence inserted in the sequence complementary to the B2c sequence, an F3 primer hav-ing a same sequence as the F3 sequence, and a B3 primer having a sequence complementary to the B3c sequence;

(6) an FIP primer having a sequence complementary to the F1 sequence on the 5'-end side and a same sequence as the F2 sequence on the 3'-end side and the tag sequence inserted in the same sequence as the F2 sequence, a BIP primer having a same sequence as the B1c sequence on the 5'-end side and a sequence complementary to the B2c sequence on the 3'-end side and the tag sequence inserted in the sequence complementary to the B2c sequence, an F3 primer having a same sequence as the F3 sequence, and a B3 primer having a sequence complementary to the B3c sequence;

(7) an FIP primer having a sequence complementary to the F1 sequence on the 5'-end side and a same sequence as the F2 sequence on the 3'-end side and the tag sequence inserted in the same sequence as the F2 sequence, a BIP primer having a same sequence as the B1c sequence on the 5'-end side and a sequence complementary to the B2c sequence on the 3'-end side, an F3 primer having a same sequence as the F3 sequence, a B3 primer having a sequence complementary to the B3c sequence, an LFc primer having a sequence complementary to the LF sequence, and an LBc primer having the same sequence as the LBc region;

(8) an FIP primer having a sequence complementary to the F1 sequence on the 5'-end side and a same sequence as the F2 sequence on the 3'-end side, a BIP primer having a same sequence as the B1c sequence on the 5'-end side and a sequence complementary to the B2c sequence on the 3'-end side and the tag sequence inserted in the sequence complementary to the B2c sequence, an F3 primer having a same sequence as the F3 sequence, a B3 primer having a sequence complementary to the B3c sequence, an LFc primer having a sequence complementary to the LF sequence, and an LBc primer having a same sequence as the LBc sequence; and (9) an FIP primer having a sequence complementary to the F1 sequence on the 5'-end side and a same sequence as the F2 sequence on the 3'-end side and the tag sequence inserted in the same sequence as the F2 sequence, a BIP primer having a same sequence as the B1c sequence on the 5'-end side and a sequence complementary to the B2c sequence on the 3'-end side and the tag sequence inserted in the sequence complementary to the B2c sequence, an F3 primer having a same sequence as the F3 sequence, a B3 primer having a sequence complementary to the B3c sequence, an LFc primer having a sequence complementary to the LF sequence, and an LBc primer having a same sequence as the LBc sequence.

5. A method of analyzing plural samples for a plurality of partial nucleic acid sequences in each sample nucleic acid of the plural samples, the sample nucleic acid comprising a plurality of template sequences for each of the partial nucleic acid sequences, to be amplified by a primer set, wherein the plurality of partial nucleic acids are different from each other, the method comprising the steps of:

(a) preparing, for each partial nucleic acid sequence, the primer set comprising a first primer and a second primer, wherein the first primer includes a first sequence, a second sequence and a tag sequence being at between the first sequence and the second sequence, the first sequence having a sequence complementary to a first part on the template sequence and the second sequence having a sequence complementary to a second part located adjacent to the first part on the template nucleic acid, wherein each tag has a sequence different from any other tag sequence, and the tag sequences are different from a complementary sequence of the sample, wherein the tag sequence is designed such that when a primer comprising the tag is bound to a template nucleic acid, the tag sequence portion loops out without binding to the template nucleic acid; and— wherein the second primer is a primer for use to amplify each of the plurality of template sequence;

(b) amplifying all of the template sequences for each of the samples in one reaction system using the primer sets to obtain an amplified product mixture, wherein the amplifying for one sample is carried out in an independent reaction system from any other reaction system for the samples, each amplified product comprising the first sequence, the second sequence and the tag sequence of the first primer;

(c) mixing the amplified product mixtures obtained for the respective samples to obtain a single mixture of the amplified product mixtures obtained in all of the independent reaction systems of (b);

(d) bringing the single mixture of (c) into a reaction with nucleic acid probes, wherein each of the nucleic acid probes have a sequence complementary to a target sequence which comprises the tag sequence, and a sequence derived from the template sequence for each of the plurality of partial nucleic acid sequences in each of the plural samples, and wherein the nucleic acid probes are immobilized on a substrate; and (e) detecting an amount of hybridization that has occurred in the step (d) so as to detect the presence or absence and/or an amount of the target nucleic acid for each partial nucleic acid sequence of each sample.

6. The method according to claim 1, wherein the amplifying by a primer set is PCR or LAMP amplification.

7. The method according to claim 3, wherein the amplifying by a primer set is PCR or LAMP.

* * * * *

SEQUENCE LISTING

<160> NUMBER OF SEQ ID NOS: 21

<210> SEQ ID NO 1
<211> LENGTH: 44
<212> TYPE: DNA
<213> ORGANISM: Artificial
<220> FEATURE:
<223> OTHER INFORMATION: primer

<400> SEQUENCE: 1
ggaagaatgt gtcagcctca aagtgaagga gaaggtgtct gcgg        44

<210> SEQ ID NO 2
<211> LENGTH: 46
<212> TYPE: DNA
<213> ORGANISM: Artificial
<220> FEATURE:
<223> OTHER INFORMATION: primer

<400> SEQUENCE: 2
ggaagaatgt gtcagcctca aagtgaagga gaaggtgtct acgcgg        46

<210> SEQ ID NO 3
<211> LENGTH: 48
<212> TYPE: DNA
<213> ORGANISM: Artificial
<220> FEATURE:
<223> OTHER INFORMATION: primer

<400> SEQUENCE: 3
ggaagaatgt gtcagcctca aagtgaagga gaaggtgtct acacgcgg        48

<210> SEQ ID NO 4
<211> LENGTH: 50
<212> TYPE: DNA
<213> ORGANISM: Artificial
<220> FEATURE:
<223> OTHER INFORMATION: primer

<400> SEQUENCE: 4
ggaagaatgt gtcagcctca aagtgaagga gaaggtgtct acacacgcgg        50

<210> SEQ ID NO 5
<211> LENGTH: 48
<212> TYPE: DNA
<213> ORGANISM: Artificial
<220> FEATURE:
<223> OTHER INFORMATION: primer

<400> SEQUENCE: 5
ggaagaatgt gtcagcctca aagtgaagga gaaggtgtct tgtggcgg        48

<210> SEQ ID NO 6
<211> LENGTH: 48
<212> TYPE: DNA
<213> ORGANISM: Artificial
<220> FEATURE:
<223> OTHER INFORMATION: primer

<400> SEQUENCE: 6
ggaagaatgt gtcagcctca aagtgaagga gaaggtgtct tctcgcgg        48

<210> SEQ ID NO 7
<211> LENGTH: 46
<212> TYPE: DNA

```
<213> ORGANISM: Artificial
<220> FEATURE:
<223> OTHER INFORMATION: primer

<400> SEQUENCE: 7
ggaagaatgt gtcagcctca aagtgaagga gaaggtgtac ctgcgg            46

<210> SEQ ID NO 8
<211> LENGTH: 48
<212> TYPE: DNA
<213> ORGANISM: Artificial
<220> FEATURE:
<223> OTHER INFORMATION: primer

<400> SEQUENCE: 8
ggaagaatgt gtcagcctca aagtgaagga gaaggtgtac acctgcgg          48

<210> SEQ ID NO 9
<211> LENGTH: 48
<212> TYPE: DNA
<213> ORGANISM: Artificial
<220> FEATURE:
<223> OTHER INFORMATION: primer

<400> SEQUENCE: 9
ggaagaatgt gtcagcctca aagtgaagga gaaggtgtac acctgcgg          48

<210> SEQ ID NO 10
<211> LENGTH: 48
<212> TYPE: DNA
<213> ORGANISM: Artificial
<220> FEATURE:
<223> OTHER INFORMATION: primer

<400> SEQUENCE: 10
ggaagaatgt gtcagcctca aagtgaagga gaaggtgttg tgctgcgg          48

<210> SEQ ID NO 11
<211> LENGTH: 48
<212> TYPE: DNA
<213> ORGANISM: Artificial
<220> FEATURE:
<223> OTHER INFORMATION: primer

<400> SEQUENCE: 11
ggaagaatgt gtcagcctca aagtgaagga gaaggtgttc tcctgcgg          48

<210> SEQ ID NO 12
<211> LENGTH: 40
<212> TYPE: DNA
<213> ORGANISM: Artificial
<220> FEATURE:
<223> OTHER INFORMATION: primer

<400> SEQUENCE: 12
caggagagcc cataagctcc cttcagcact ccacccagag                   40

<210> SEQ ID NO 13
<211> LENGTH: 18
<212> TYPE: DNA
<213> ORGANISM: Artificial
<220> FEATURE:
<223> OTHER INFORMATION: primer

<400> SEQUENCE: 13
gttaccccaa aggccacc                                           18
```

-continued

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
tctgggaaga actcagcgaa                                               20

<210> SEQ ID NO 15
<211> LENGTH: 21
<212> TYPE: DNA
<213> ORGANISM: Artificial
<220> FEATURE:
<223> OTHER INFORMATION: primer

<400> SEQUENCE: 15
ccgcaccgtc ctcgcacagg c                                             21

<210> SEQ ID NO 16
<211> LENGTH: 14
<212> TYPE: DNA
<213> ORGANISM: Artificial
<220> FEATURE:
<223> OTHER INFORMATION: probe

<400> SEQUENCE: 16
gtgctgcagg tgcg                                                     14

<210> SEQ ID NO 17
<211> LENGTH: 18
<212> TYPE: DNA
<213> ORGANISM: Artificial
<220> FEATURE:
<223> OTHER INFORMATION: probe

<400> SEQUENCE: 17
ctacacgcgg gagccgat                                                 18

<210> SEQ ID NO 18
<211> LENGTH: 18
<212> TYPE: DNA
<213> ORGANISM: Artificial
<220> FEATURE:
<223> OTHER INFORMATION: probe

<400> SEQUENCE: 18
cttgtggcgg gagccgat                                                 18

<210> SEQ ID NO 19
<211> LENGTH: 18
<212> TYPE: DNA
<213> ORGANISM: Artificial
<220> FEATURE:
<223> OTHER INFORMATION: probe

<400> SEQUENCE: 19
cttctcgcgg gagccgat                                                 18

<210> SEQ ID NO 20
<211> LENGTH: 18
<212> TYPE: DNA
<213> ORGANISM: Artificial
<220> FEATURE:
<223> OTHER INFORMATION: probe

```
<400> SEQUENCE: 20
ctacacgcgg gaggcgat                                                       18

<210> SEQ ID NO 21
<211> LENGTH: 540
<212> TYPE: DNA
<213> ORGANISM: Human

<400> SEQUENCE: 21
gctgttggaa ggtgcaagat cagagccccc aaagcagagg actctctctg cccagtccct         60
gtggtctctt catccctcgc cttgaacagg tggaggccag cctctcctga ctgtcatccc        120
tattggcagg ttaccccaaa ggccaccccg aagcagggag ctttgaggct gacctgaagc        180
acttgaagga gaaggtgtct gcgggagccg atttcatcat cacgcagctt ttctttgagg        240
ctgacacatt cttccgcttt gtgaaggcat gcaccgacat gggcatcact tgccccatcg        300
tccccgggat ctttcccatc caggtgaggg gcccaggaga gcccataagc tccctccacc        360
ccactctcac cgcaccgtcc tcgcacaggc tgggggctct gggtggagtg ctgagttcgc        420
tgagttcttc ccagatctcc tctcaggtcc agaacttgca cagcgttgct tggccacccc        480
attttggtta cctctaattt tcccccaaa acccagcaac agtgtctgtt gaggggtttg         540
```